US009909123B2

(12) United States Patent
Malone et al.

(10) Patent No.: US 9,909,123 B2
(45) Date of Patent: Mar. 6, 2018

(54) ANTISENSE MOLECULES FOR TREATMENT OF *STAPHYLOCOCCUS AUREUS* INFECTION

(71) Applicant: Techulon Inc., Blacksburg, VA (US)

(72) Inventors: Brett Malone, Pearisburg, VA (US); Joshua Bryson, Blacksburg, VA (US)

(73) Assignee: Techulon Inc., Blacksburg, VA (US)

( * ) Notice: Subject to any disclaimer, the term of this patent is extended or adjusted under 35 U.S.C. 154(b) by 24 days.

(21) Appl. No.: 14/777,007

(22) PCT Filed: Mar. 14, 2014

(86) PCT No.: PCT/US2014/028830
§ 371 (c)(1),
(2) Date: Sep. 15, 2015

(87) PCT Pub. No.: WO2014/144423
PCT Pub. Date: Sep. 18, 2014

(65) Prior Publication Data
US 2016/0177297 A1 Jun. 23, 2016

Related U.S. Application Data

(60) Provisional application No. 61/786,926, filed on Mar. 15, 2013.

(51) Int. Cl.
*C12N 15/11* (2006.01)
*C12N 15/113* (2010.01)
*A61K 9/00* (2006.01)
*A61K 31/7088* (2006.01)
*A61K 47/64* (2017.01)

(52) U.S. Cl.
CPC .......... *C12N 15/113* (2013.01); *A61K 9/0014* (2013.01); *A61K 31/7088* (2013.01); *A61K 47/64* (2017.08); *C12N 2310/11* (2013.01); *C12N 2310/111* (2013.01); *C12N 2310/3181* (2013.01); *C12N 2310/3513* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 5,116,195 A | 5/1992 | Pattarozzi | |
| 5,521,291 A | 5/1996 | Curiel et al. | |
| 5,527,675 A | 6/1996 | Coull et al. | |
| 5,539,082 A | 7/1996 | Nielsen et al. | |
| 5,623,049 A | 4/1997 | Loebberding et al. | |
| 5,652,211 A | 7/1997 | Porro | |
| 5,714,331 A | 2/1998 | Buchardt et al. | |
| 5,736,336 A | 4/1998 | Buchardt et al. | |
| 5,773,571 A | 6/1998 | Nielsen et al. | |
| 5,786,461 A | 7/1998 | Buchardt et al. | |
| 5,811,232 A | 9/1998 | Crooke et al. | |
| 5,837,459 A | 11/1998 | Berg et al. | |
| 5,874,564 A | 2/1999 | Ecker et al. | |
| 5,891,625 A | 4/1999 | Buchardt et al. | |
| 5,972,610 A | 10/1999 | Buchardt et al. | |
| 5,986,053 A | 11/1999 | Ecker et al. | |
| 6,107,470 A | 8/2000 | Nielsen et al. | |
| 6,174,870 B1 | 1/2001 | Crooke et al. | |
| 6,589,738 B1 * | 7/2003 | Forsyth ............... C07K 14/245 435/5 |
| 6,593,114 B1 | 7/2003 | Kunsch et al. | |
| 6,713,602 B1 | 3/2004 | Buchardt et al. | |
| 7,098,192 B2 | 8/2006 | Karras | |
| 7,696,345 B2 | 4/2010 | Allerson et al. | |
| 7,875,733 B2 | 1/2011 | Bhat et al. | |
| 7,879,813 B2 | 2/2011 | Chatterton | |
| 7,919,612 B2 | 4/2011 | Baker et al. | |
| 7,939,677 B2 | 5/2011 | Bhat et al. | |
| 7,943,581 B2 | 5/2011 | Divita et al. | |
| 8,039,587 B2 | 10/2011 | Khan | |
| 8,044,019 B2 | 10/2011 | Uno et al. | |
| 8,110,198 B2 | 2/2012 | Stamm-Doucette et al. | |
| 8,124,745 B2 | 2/2012 | Allerson et al. | |
| 8,138,383 B2 | 3/2012 | Wakefield et al. | |
| 8,207,293 B2 | 6/2012 | Ronjat et al. | |

(Continued)

FOREIGN PATENT DOCUMENTS

| | | | | |
|---|---|---|---|---|
| JP | 2007505697 A | 3/2007 | | |
| JP | 2012523451 A | 10/2012 | | |
| WO | WO-200011184 | 3/2000 | | |
| WO | WO 01/34810 A2 | 5/2001 | | |
| WO | WO-2005027990 A2 | 3/2005 | | |
| WO | WO 2005042708 A2 * | 5/2005 | ........... C12N 15/111 |
| WO | WO-2007/009094 A2 | 1/2007 | | |
| WO | WO-2007048046 A2 | 4/2007 | | |
| WO | WO-2010011895 A1 | 1/2010 | | |
| WO | WO-2010119385 A1 | 10/2010 | | |
| WO | WO-2012174543 A2 | 12/2012 | | |
| WO | WO-2014144442 A2 | 9/2014 | | |
| WO | WO-2014197091 A2 | 12/2014 | | |

OTHER PUBLICATIONS

Young et al, Discovery of FabH/FabF Inhibitors from Natural Products, 2006, Antimicrobial Agents and Chemotherapy, vol. 50, 2: 519-526.*

(Continued)

*Primary Examiner* — Ekaterina Poliakova-Georgantas
(74) *Attorney, Agent, or Firm* — Sterne, Kessler, Goldstein & Fox P.L.L.C.

(57) ABSTRACT

Disclosed are antisense molecules and compositions for the treatment of *Staphylococcus aureus* infection. The antisense molecules and compositions comprise nucleic acid molecules, such as RNA, DNA, or nucleic acid molecules with modified backbones, such as PNA. The antisense molecules and compositions inhibit gene expression in *Staphylococcus aureus*; are optionally conjugated to cell penetration molecules such as peptides; and are optionally administered in the form of a nanoparticle composition.

14 Claims, 3 Drawing Sheets

(56) References Cited

U.S. PATENT DOCUMENTS

| | | | |
|---|---|---|---|
| 8,211,468 B2 | 7/2012 | Rozema et al. | |
| 8,242,081 B2 | 8/2012 | Divita et al. | |
| 8,299,236 B2 | 10/2012 | Chen et al. | |
| 8,313,778 B2 | 11/2012 | Seiler et al. | |
| 8,314,229 B2 | 11/2012 | Khvorova et al. | |
| 8,338,366 B2 | 12/2012 | Lin et al. | |
| 8,354,093 B2 | 1/2013 | Becker et al. | |
| 8,354,387 B2 | 1/2013 | Divita et al. | |
| 8,357,664 B2 | 1/2013 | Stein et al. | |
| 8,362,221 B2 | 1/2013 | Berka et al. | |
| 8,372,969 B2 | 2/2013 | Ying et al. | |
| 8,377,898 B2 | 2/2013 | Kandimalla et al. | |
| 2004/0097718 A1 | 5/2004 | Pearson et al. | |
| 2005/0026189 A1 | 2/2005 | Wang et al. | |
| 2005/0131215 A1 | 6/2005 | Slightom | |
| 2005/0246794 A1* | 11/2005 | Khvorova | A61K 31/713 800/286 |
| 2006/0024814 A1* | 2/2006 | Peters | C07H 21/00 435/287.2 |
| 2007/0135372 A1* | 6/2007 | MacLachlan | C12N 15/113 514/44 A |
| 2009/0105115 A1 | 4/2009 | Reineke | |
| 2009/0119022 A1 | 5/2009 | Timberlake | |
| 2009/0124534 A1 | 5/2009 | Reineke | |
| 2010/0099186 A1* | 4/2010 | Perry | C12N 5/0647 435/373 |
| 2010/0233141 A1* | 9/2010 | Polach | C12N 15/63 424/93.7 |
| 2012/0040409 A1 | 2/2012 | Hau et al. | |
| 2012/0122769 A1 | 5/2012 | Iversen | |
| 2016/0003835 A1* | 1/2016 | Halbert | C12N 15/115 506/9 |

OTHER PUBLICATIONS

Altschul, S.F., "Amino Acid Substitution Matrices from an Information Theoretic Perspective," *Journal of Molecular Biology* 219(3):555-565, Elsevier, England (1991).

Berge, S.M., et al., "Pharmaceutical Salts," *Journal of Pharmaceutical Sciences* 66(1):1-19, Wiley, United States (1977).

Dirksen, A., et al., "Nucleophilic Catalysis of Hydrazone Formation and Transimination: Implications for Dynamic Covalent Chemistry," *Journal of the American Chemical Society* 128(49):15602-15603, American Chemical Society, United States (2006).

Fernandez-Lopez, S., et al., "Antibacterial Agents Based on the Cyclic D,L-a-α-peptide Architecture," *Nature* 412:452-455, Nature Publishing Company, United States (2001).

Haste, N.M., et al., "Activity of the Streptogramin Antibiotic Etamycin Against Methicillin-resistant *Staphylococcus aureus*," *The Journal of Antibiotics* 63(5):219-224, Nature Publishing Group, Japan (2010).

Hemp, S.T., et al., "Phosphonium-Containing Diblock Copolymers for Enhanced Colloidal Stability and Efficient Nucleic Acid Delivery," *Biomacromolecules* 13(8):2439-2445, American Chemical Society, United States (2012).

Henikoff, S. and Henikoff, J.G., "Amino Acid Substitution Matrices from Protein Blocks," *Proceedings of the National Academy of Sciences USA* 89(22):10915-10919, National Academy of Sciences, United States (1992).

Koshkin, A.A., et al., "LNA (Locked Nucleic Acids): Synthesis of the Adenine, Cytosine, Guanine, 5-methylcytosine, Thymine and Uracil Bicyclonucleoside Monomers, Oligomerisation and Unprecedented Nucleic Acid Recognition," *Tetrahedron* 54:3607-3630, Elsevier, England (1998).

Nekhotiaeva, N., et al., "Cell Entry and Antimicrobial Properties of Eukaryotic Cell-penetrating Peptides," *FASEB Journal* 18(2):394-396, The Federation, United States (2004).

Nekhotiaeva, N., et al., "Inhibition of *Staphylococcus aureus* Gene Expression and Growth Using Antisense Peptide Nucleic Acids," *Molecular Therapy* 10(4):652-659, Academic Press, United States (2004).

Tachi, T., et al., "Position-dependent Hydrophobicity of the Antimicrobial Magainin Peptide Affects the Mode of Peptide-lipid Interactions and Selective Toxicity," *Biochemistry* 41(34):10723-10731, American Chemical Society, United States (2002).

Thompson, J.D., et al., "Clustal W: Improving the Sensitivity of Progressive Multiple Sequence Alignment Through Sequence Weighting, Position-specific Gap Penalties and Weight Matrix Choice," *Nucleic Acids Research* 22(22):4673-4680, Oxford University Press, England (1994).

Tranter, M., et al., "In Vivo Delivery of Nucleic Acids via Glycopolymer Vehicles Affords Therapeutic Infarct Size Reduction in Vivo," *Molecular Therapy* 20(3):601-608, Academic Press, United States (2012).

Wagner, E., et al., "A Simple Procedure for the Preparation of Protected 2'-O-methyl or 2'-O-ethyl Ribonucleoside-3'-O-phosphoramidites," *Nucleic Acids Research* 19(21):5965-5971, Oxford University Press, England (1991).

Wikler, M., et al., "Methods for Dilution Antimicrobial Susceptibility Tests for Bacteria that Grow Aerobically, Approved Standard—Seventh Edition," *Clinical and Laboratory Standards Institute* 26(2):M7- A7, Clinical and Laboratory Standards Institute, United States (2006).

Wongrakpanich, A., et al., "Poly(galactaramidoamine) is an Efficient Cationic Polymeric Non-viral Vector with Low Cytotoxicity for Transfecting Human Embryonic Kidney (HEK293) and Murine Macrophage (RAW264.7) Cells," *Pharmaceutical Development and Technology* 18(5):1255-1258, Informa Healthcare, England (2012).

International Search Report and Written Opinion, International Application No. PCT/US2014/028830, dated Sep. 10, 2014.

Co-pending U.S. Appl. No. 14/777,002, inventor Malone, B., I.A., filed Mar. 14, 2014.

Co-pending U.S. Appl. No. 14/777,011, inventor Malone, B., I.A., filed Mar. 14, 2014.

Zhang, C. et al., "Discovery of okilactomycin and congeners from *Streptomyces scabrisporus* by antisense differential sensitivity assay targeting ribosomal protein S4," *J. Antibiotics* 62:55-61 (2009) (Nature Publishing Group, New York, NY).

Bai, H. et al., "Targeting RNA polymerase primary σ70 as a therapeutic strategy against methicillin-resistant *Staphylococcus aureus* by antisense peptide nucleic acid," *Plos ONE* 7(1):1-10 (2012) (Public Library of Science, San Francisco, CA).

* cited by examiner

SEQUENCE LISTING

```
<160> NUMBER OF SEQ ID NOS: 101

<210> SEQ ID NO 1
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 1
tttcatttcg gcacc                                                      15
```

-continued

```
<210> SEQ ID NO 2
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 2
cgctcacttt tgtaa                                                    15

<210> SEQ ID NO 3
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 3
acgaggcata at                                                       12

<210> SEQ ID NO 4
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 4
tgtttaccca ta                                                       12

<210> SEQ ID NO 5
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 5
aacatcggaa tg                                                       12

<210> SEQ ID NO 6
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 6
actcgtggca ta                                                       12

<210> SEQ ID NO 7
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 7
cgagccataa ta                                                       12

<210> SEQ ID NO 8
<211> LENGTH: 12
<212> TYPE: DNA
<213> ORGANISM: Artificial Sequence
<220> FEATURE:
<223> OTHER INFORMATION: synthetic antisense strand
```

```
<400> SEQUENCE: 8
acgcataata at                                                              12

<210> SEQ ID NO 9
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 9
ttacgtgcca tt                                                              12

<210> SEQ ID NO 10
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 10
tacgtgccat at                                                              12

<210> SEQ ID NO 11
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 11
cgagccatgt at                                                              12

<210> SEQ ID NO 12
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 12
tcatgttatg gc                                                              12

<210> SEQ ID NO 13
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 13
gttggatcat ta                                                              12

<210> SEQ ID NO 14
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 14
tctttcgctc ac                                                              12

<210> SEQ ID NO 15
<211> LENGTH: 12
```

```
<212> TYPE: DNA
<213> ORGANISM: Artificial Sequence
<220> FEATURE:
<223> OTHER INFORMATION: synthetic antisense strand

<400> SEQUENCE: 15
tacgagccat tt                                                            12

<210> SEQ ID NO 16
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 16
tagccattgt cg                                                            12

<210> SEQ ID NO 17
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 17
catcgaaagt cc                                                            12

<210> SEQ ID NO 18
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 18
gttctcattt tatat                                                         15

<210> SEQ ID NO 19
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 19
tagccacgat gtgca                                                         15

<210> SEQ ID NO 20
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 20
ttagccattt atagt                                                         15

<210> SEQ ID NO 21
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 21
```
agacattcag acacc                                                    15

<210> SEQ ID NO 22
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 22
gttggcatgt gatat                                                    15

<210> SEQ ID NO 23
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 23
tttacgaggc ataat                                                    15

<210> SEQ ID NO 24
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 24
tactgccatg atata                                                    15

<210> SEQ ID NO 25
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 25
tgatttgtca ttata                                                    15

<210> SEQ ID NO 26
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 26
tatactcatt ttggg                                                    15

<210> SEQ ID NO 27
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 27
aaattgccat aatca                                                    15

<210> SEQ ID NO 28
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 28
tttagacatc tgtat                                                    15

<210> SEQ ID NO 29
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 29
taacatcgga atgca                                                    15

<210> SEQ ID NO 30
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 30
cagtaatcat aataa                                                    15

<210> SEQ ID NO 31
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 31
agcaaacata ctttg                                                    15

<210> SEQ ID NO 32
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 32
gagccataat aagac                                                    15

<210> SEQ ID NO 33
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 33
ttgacgcata ataat                                                    15

<210> SEQ ID NO 34
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 34
tttacgtgcc attta                                                    15

```
<210> SEQ ID NO 35
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 35
tacgtgccat attaa                                                15

<210> SEQ ID NO 36
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 36
tttagccata actag                                                15

<210> SEQ ID NO 37
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 37
cgagccatgt atttg                                                15

<210> SEQ ID NO 38
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 38
gatcatttca atact                                                15

<210> SEQ ID NO 39
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 39
actcatgtta tggca                                                15

<210> SEQ ID NO 40
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 40
tttagccact taatt                                                15

<210> SEQ ID NO 41
<211> LENGTH: 15
<212> TYPE: DNA
<213> ORGANISM: Artificial Sequence
<220> FEATURE:
<223> OTHER INFORMATION: synthetic antisense strand
```

<400> SEQUENCE: 41
cggttcaaag tggga                                                          15

<210> SEQ ID NO 42
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 42
tggatcatta gttaa                                                          15

<210> SEQ ID NO 43
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 43
ggtagtaaca ttatt                                                          15

<210> SEQ ID NO 44
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 44
ttgacccaca gtatt                                                          15

<210> SEQ ID NO 45
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 45
ttccattagg atgtc                                                          15

<210> SEQ ID NO 46
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 46
gagccatttg ggcgc                                                          15

<210> SEQ ID NO 47
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 47
agccattgtc gctta                                                          15

<210> SEQ ID NO 48

```
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 48
ttccattatc cgagc                                                      15

<210> SEQ ID NO 49
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 49
ggtcatcgaa agtcc                                                      15

<210> SEQ ID NO 50
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 50
gttttaccat gcaaa                                                      15

<210> SEQ ID NO 51
<211> LENGTH: 10
<212> TYPE: PRT
<213> ORGANISM: Artificial Sequence
<220> FEATURE:
<223> OTHER INFORMATION: peptide

<400> SEQUENCE: 51

Lys Phe Phe Lys Phe Phe Lys Phe Phe Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: peptide

<400> SEQUENCE: 52

Arg Phe Phe Arg Phe Phe Arg Phe Phe Arg
1               5                   10

<210> SEQ ID NO 53
<211> LENGTH: 23
<212> TYPE: PRT
<213> ORGANISM: Artificial Sequence
<220> FEATURE:
<223> OTHER INFORMATION: peptide

<400> SEQUENCE: 53

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 54
<211> LENGTH: 21
```

```
<212> TYPE: PRT
<213> ORGANISM: Artificial Sequence
<220> FEATURE:
<223> OTHER INFORMATION: peptide

<400> SEQUENCE: 54

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 55
<211> LENGTH: 6
<212> TYPE: PRT
<213> ORGANISM: Artificial Sequence
<220> FEATURE:
<223> OTHER INFORMATION: peptide

<400> SEQUENCE: 55

Lys Lys Leu Trp Leu Trp
1               5

<210> SEQ ID NO 56
<211> LENGTH: 8
<212> TYPE: PRT
<213> ORGANISM: Artificial Sequence
<220> FEATURE:
<223> OTHER INFORMATION: peptide

<400> SEQUENCE: 56

Arg Arg Lys Trp Leu Trp Leu Trp
1               5

<210> SEQ ID NO 57
<211> LENGTH: 8
<212> TYPE: PRT
<213> ORGANISM: Artificial Sequence
<220> FEATURE:
<223> OTHER INFORMATION: peptide

<400> SEQUENCE: 57

Lys Gln Arg Trp Leu Trp Leu Trp
1               5

<210> SEQ ID NO 58
<211> LENGTH: 18
<212> TYPE: PRT
<213> ORGANISM: Artificial Sequence
<220> FEATURE:
<223> OTHER INFORMATION: peptide

<400> SEQUENCE: 58

Leu Leu Ile Ile Leu Arg Arg Arg Ile Arg Lys Gln Ala His Ala His
1               5                   10                  15

Ser Lys

<210> SEQ ID NO 59
<211> LENGTH: 16
<212> TYPE: PRT
<213> ORGANISM: Artificial Sequence
<220> FEATURE:
<223> OTHER INFORMATION: peptide

<400> SEQUENCE: 59

Arg Gln Ile Lys Ile Trp Phe Gln Asn Arg Arg Met Lys Trp Lys Lys
1               5                   10                  15
```

-continued

<210> SEQ ID NO 60
<211> LENGTH: 12
<212> TYPE: PRT
<213> ORGANISM: Artificial Sequence
<220> FEATURE:
<223> OTHER INFORMATION: peptide

<400> SEQUENCE: 60

Gly Arg Lys Lys Arg Arg Gln Arg Arg Arg Pro Gln
1               5                   10

<210> SEQ ID NO 61
<211> LENGTH: 13
<212> TYPE: PRT
<213> ORGANISM: Artificial Sequence
<220> FEATURE:
<223> OTHER INFORMATION: peptide

<400> SEQUENCE: 61

Ile Leu Pro Trp Lys Trp Pro Trp Trp Pro Trp Arg Arg
1               5                   10

<210> SEQ ID NO 62
<211> LENGTH: 15
<212> TYPE: DNA
<213> ORGANISM: Artificial Sequence
<220> FEATURE:
<223> OTHER INFORMATION: peptide

<400> SEQUENCE: 62
ttttccatga tttat                                                     15

<210> SEQ ID NO 63
<211> LENGTH: 15
<212> TYPE: DNA
<213> ORGANISM: Artificial Sequence
<220> FEATURE:
<223> OTHER INFORMATION: noncoding peptide

<400> SEQUENCE: 63
aacattttgg ttttt                                                     15

<210> SEQ ID NO 64
<211> LENGTH: 12
<212> TYPE: DNA
<213> ORGANISM: Artificial Sequence
<220> FEATURE:
<223> OTHER INFORMATION: peptide

<400> SEQUENCE: 64
tccatgattt at                                                        12

<210> SEQ ID NO 65
<211> LENGTH: 501
<212> TYPE: DNA
<213> ORGANISM: Staphylococcus aureus

<400> SEQUENCE: 65
atgtctgcta tcattgaagc taaaaaacaa ctagttgatg aaattgctga ggtactatca     60
aattcagttt caacagtaat cgttgactat cgtggattaa cagtagctga agttactgac    120
ttacgttcac aattacgtga agctggtgtt gagtataaag tatacaaaaa cactatggta    180
cgtcgtgcag ctgaaaaagc tggtatcgaa ggcttagatg aattcttaac aggtcctact    240

```
gctattgcaa cttcaagtga agatgctgta gctgcagcga aagtaatttc tggatttgct      300
aaagatcatg aagcattaga aattaaatca ggtgttatgg aaggcaatgt tattacagca      360
gaagaagtta aaactgttgg ttcattacct tcacacgatg gtcttgtatc tatgctttta      420
tcagtattac aagctcctgt acgcaacttc gcttatgcgg ttaaagctat tggagaacaa      480
aaagaagaaa acgctgaata a                                                501

<210> SEQ ID NO 66
<211> LENGTH: 423
<212> TYPE: DNA
<213> ORGANISM: Staphylococcus aureus

<400> SEQUENCE: 66
gtggctaaaa aagtagataa agttgttaaa ttacaaattc ctgcaggtaa agcgaatcca       60
gcaccaccag ttggtccagc attaggtcaa gcaggtgtga acatcatggg attctgtaaa      120
gagttcaatg cacgtactca agatcaagca ggtttaatta ttccggtaga aatcagtgtt      180
tatgaagatc gttcatttac atttattaca aaaactccac cggctccagt attacttaaa      240
aaagcagctg gtattgaaaa aggttcaggc gaaccaaaca aaactaaagt tgctacagta      300
actaaagatc aagtacgcga aattgctaac agcaaaatgc aagacttaaa cgctgctgac      360
gaagaagcag ctatgcgtat tatcgaaggt actgcacgta gtatgggtat cgttgtagaa      420
taa                                                                    423

<210> SEQ ID NO 67
<211> LENGTH: 438
<212> TYPE: DNA
<213> ORGANISM: Staphylococcus aureus

<400> SEQUENCE: 67
atgcgtcaaa catttatggc aaatgaatca acattgagc gcaaatggta tgttatcgat        60
gctgaaggcc aaacattagg tcgtttatca tcagaagtag catctatctt acgcggtaaa      120
aataaagtaa cttacacacc acacgttgat actggtgatt atgtaatcgt tattaatgca      180
tcaaaaatcg aatttactgg taacaaagaa actgacaaag tttactaccg tcactcaaat      240
catccaggtg gtatcaaatc aatcactgct ggtgaattaa gaagaactaa cccagaacgt      300
ttaattgaaa actcaattaa aggtatgtta ccaagcactc gtttaggcga aaaacaaggt      360
aaaaaattat ttgtatatgg tggcgctgaa catccacacg ctgcacaaca accagaaaac      420
tacgaattac gtggttaa                                                    438

<210> SEQ ID NO 68
<211> LENGTH: 369
<212> TYPE: DNA
<213> ORGANISM: Staphylococcus aureus

<400> SEQUENCE: 68
atgatccaac aagaaacacg cttgaaagta gcagacaact ctggtgctcg tgaagttctt       60
acaatcaaag tattaggtgg atctggtcgt aaaacagcaa acatcggcga tgttatcgta      120
tgtactgtta aaaatgcaac accaggtggc gttgttaaaa aaggtgacgt tgtcaaagct      180
gtaatcgtac gtactaagtc aggtgttcgt cgtaatgacg gttcatacat caaatttgat      240
gaaaatgcat gtgttatcat ccgtgatgac aaaggcccac gtggtactcg tatcttcgga      300
cctgttgctc gtgaattacg tgaaggtaac ttcatgaaaa tcgtatcatt agcaccagaa      360
gtactttaa                                                              369
```

<210> SEQ ID NO 69
<211> LENGTH: 441
<212> TYPE: DNA
<213> ORGANISM: Staphylococcus aureus

<400> SEQUENCE: 69

```
atgaaattac atgagttaaa accggcagaa ggttcacgta agaacgcaa tcgtgttgga      60
cgtggtgttg cgacaggtaa tggtaaaaca gtggtcgcg acacaaagg tcaaaaagct     120
cgttcaggcg gtggtgtaag accaggattt gaaggtggtc aattaccatt attccgtcgt    180
ttaccaaaac gtggttttac taacataaat cgtaaagaat atgctattgt taacttagac    240
caacttaata aatttgaaga tggtactgaa gtaactccag ctttattagt agaatctggt    300
gttgttaaga atgaaaaatc tggtatcaaa atactaggta atggttcact tgataagaaa    360
ttgacagtga aagctcataa attctcagct tcagcagcag aagctattga tgctaaaggt    420
ggagcacacg aggtgatcta a                                              441
```

<210> SEQ ID NO 70
<211> LENGTH: 434
<212> TYPE: DNA
<213> ORGANISM: Staphylococcus aureus

<400> SEQUENCE: 70

```
atgttactac caaaacgtgt aaaatatcgt cgtcaacatc gtcctaaaac aactggtcgt      60
tctaaaggcg gtaactacgt aacatttggt gagtttggtt tacaagctac aacaacgtct    120
tggatcacat ctcgtcaaat cgaatctgct cgtatagcaa tgacacgtta catgaaacgt    180
ggcgggaaag tttggattaa aatcttccca catacaccat atactaaaaa acctttagaa    240
gtacgtatgg gtgctggtaa aggtgcggtt gaaggctgga tcgcagttgt taaaccaggt    300
agaattttat tcgaagttgc tggcgtttct gaagagttgc gcgtgaagca ctacgtttag    360
caagtcacaa acttccagta aaaactaagt ttgtaaaacg tgaggaattg ggtggtgaaa    420
caaatgaaag ctaa                                                      434
```

<210> SEQ ID NO 71
<211> LENGTH: 360
<212> TYPE: DNA
<213> ORGANISM: Staphylococcus aureus

<400> SEQUENCE: 71

```
atgatcagta aaattgataa aaataaagtg cgtttaaaaa gacatgctcg tgttcgtact      60
aacttatcag gtacagctga aaagccacgt ttaaacgtat atcgttcaaa caagcatatc    120
tacgctcaaa ttattgatga taataaaggc gtaacattag ctcaagcttc ttcaaaagac    180
agcgacattg ctactacagc aactaaagtt gaattagcaa ctaaagtcgg tgaagcaatt    240
gctaaaaaag ctgctgacaa aggcattaaa gaaatcgtat ttgaccgtgg aggatattta    300
tatcacggac gtgttaaagc attagctgaa gcagcaagag aaagcggatt agaattttaa    360
```

<210> SEQ ID NO 72
<211> LENGTH: 351
<212> TYPE: DNA
<213> ORGANISM: Staphylococcus aureus

<400> SEQUENCE: 72

```
atgacaaatc acaaattaat cgaagcagta actaaatcac aattgcgtac agacttacca      60
```

```
agtttccgtc ctggtgatac tttacgtgta cacgtacgta tcattgaggg tactcgtgag    120
cgtatccaag tattcgaagg cattgtaatt aaacgtcgtg gcggtggcgt ttctgaaacg    180
tttacagttc gtaaaatttc atcaggtgtt ggcgtggaac gtacattccc attacacaca    240
ccaaaaattg aaaaaatcga agttaaacgt cgtggtaaag tacgtcgtgc taaattatat    300
tacttacgta gtttacgtgg taaagctgct agaatccaag aaattcgtta a             351
```

<210> SEQ ID NO 73
<211> LENGTH: 693
<212> TYPE: DNA
<213> ORGANISM: Staphylococcus aureus

<400> SEQUENCE: 73

```
atggctaaaa aaggtaaaaa gtatcaagaa gcagctagta aagttgaccg tactcagcac     60
tacagtgttg aagaagcaat taaattagct aaagaaacaa gcattgctaa ctttgacgct    120
tctgttgaag ttgcattccg tttaggaatt gatacacgta aaaatgacca acaaatccgt    180
ggtgcagttg tattaccaaa cggaactggt aaatcacaaa gtgtattagt attcgctaaa    240
ggtgacaaaa ttgctgaagc tgaagcagca ggtactgact atgtaggtga agcagaatac    300
gttcaaaaaa tccaacaagg ttggttcgac ttcgatgtag tagttgctac accagacatg    360
atgggtgaag ttggtaaatt aggtcgtgta ttaggaccaa aaggttttaat gccaaaccct    420 aaaactggaa ctgtaacaat ggatgttaaa aaagctgttg aagaaatcaa agctggtaaa    480
gtagaatatc gtgctgaaaa agctggtatc gtacatgcat caattggtaa agtttcattt    540
actgatgaac aattaattga aaacttcaat actttacaag atgtattagc taaagctaaa    600
ccatcatctg ctaaaggtac atacttcaaa tctgttgctg taactacaac aatgggtcct    660
ggagttaaaa ttgatactgc aagtttcaaa taa                                 693
```

<210> SEQ ID NO 74
<211> LENGTH: 357
<212> TYPE: DNA
<213> ORGANISM: Staphylococcus aureus

<400> SEQUENCE: 74

```
atgccacgag ttaaaggtgg aacagtaaca agagcgcgtc gtaaaaaaac gattaaatta     60
gctaaaggtt acttcggttc aaaacataca ttatacaaag tagctaagca acaagtaatg    120
aaatcaggtc aatatgcttt ccgtgaccgt cgtcaacgta acgtgacttt ccgtaaatta    180
tggattacac gtatcaacgc agcagctcgt caacatgaaa tgagctactc acgtttaatg    240
aacggtttga aaaaagctgg tatcgacatt aaccgtaaaa tgttatcaga atcgcaatt    300 tctgacgaaa aagcatttgc tcaattagta actaaagcta agatgctttt aaaataa      357
```

<210> SEQ ID NO 75
<211> LENGTH: 309
<212> TYPE: DNA
<213> ORGANISM: Staphylococcus aureus

<400> SEQUENCE: 75

```
atgtttgcta ttattgaaac aggtggaaaa caaatcaaag tagaagaagg tcaagaaatc     60
ttcgttgaaa aattagacgt aaacgaagga gatacttta catttgataa agtattattt    120
gtaggtggag attcagttaa agttggagcg ccaacagttg aaggtgcaac agttactgct    180
actgttaata aacaaggtcg cggtaaaaaa atcactgtat tcacatacaa acgtcgtaaa    240
aattcaaaac gtaaaaaagg ccatcgtcaa ccatacacta aattaacaat cgataaaatc    300
``` aacgcgtaa											309

<210> SEQ ID NO 76
<211> LENGTH: 354
<212> TYPE: DNA
<213> ORGANISM: Staphylococcus aureus

<400> SEQUENCE: 76
atggaagcaa aagcggttgc tagaacaata agaatcgcac ctcgtaaagt aagactagtt      60
cttgacttaa tcagaggtaa aaatgctgct gaagctattg caattttaaa attaacaaac     120
aaagcttcat caccagtaat tgaaaaagta ttaatgtccg ctttagctaa tgctgaacat     180
aactatgaca tgaacacaga tgaattagta gttaaagaag catatgctaa cgaaggacca     240
acattaaaac gtttccgtcc acgtgcgcaa ggtcgtgcaa gtgcgattaa caaacgtaca     300
agccacatta caatcgtcgt aagtgacggt aaagaagaag ctaagaagc ttaa            354

<210> SEQ ID NO 77
<211> LENGTH: 276
<212> TYPE: DNA
<213> ORGANISM: Staphylococcus aureus

<400> SEQUENCE: 77
atggaagcaa gagatattct taagcgcccc gtaatcactg agaaatcttc tgaagcaatg      60
gctgaagaca atacacttt cgacgttgat actcgtgtta acaaaacaca agtaaaaatg     120
gcagttgaag aaatcttcaa cgtaaaagtt gcaagtgtta atatcatgaa ttacaaacct     180
aagaaaaaac gtatgggccg ttaccaaggc tatacaaaca aagaagaaa agcgattgta     240 actcttaaag aaggatcaat cgacttattt aactaa                              276

<210> SEQ ID NO 78
<211> LENGTH: 285
<212> TYPE: DNA
<213> ORGANISM: Staphylococcus aureus

<400> SEQUENCE: 78
atgttaaaat taaacttaca attcttcgca tctaaaaaag gggtaagttc tacaaaaaac      60
ggacgtgact ctgaatcaaa acgcttaggt gctaaacgtg ctgacggtca attcgtaaca     120
ggtggttcaa ttttatatcg ccaacgtggt actaaaattt accctggtga aaatgtaggt     180
cgtggtggcg atgatacatt attcgctaaa atcgacggcg ttgttaaatt cgaacgtaaa     240
ggtcgcgaca aaaaacaagt ttctgtatat gcagtagctg aataa                    285

<210> SEQ ID NO 79
<211> LENGTH: 189
<212> TYPE: DNA
<213> ORGANISM: Staphylococcus aureus

<400> SEQUENCE: 79
atgggtaaac aatgtttcgt aacaggtcgt aaagcttcga ctggtaacag acgttcacac      60
gctttaaact ctactaaacg tagatggaac gctaaccttc aaaaagttag aatcctagtt     120
gacggtaaac ctaaaaaagt ttgggttct gcacgtgctt taaatctgg taaagtaact     180 agagtttaa                                                            189

<210> SEQ ID NO 80
<211> LENGTH: 834
<212> TYPE: DNA

<213> ORGANISM: Staphylococcus aureus

<400> SEQUENCE: 80

| | | |
|---|---|---|
| atggctatta aaaagtataa gccaataaca atggtcgtc gtaatatgac ttcgttagat | 60 |
| ttcgcagaaa tcacgaaaac tacacctgaa aagtcattat taaaaccgct accgaaaaaa | 120 |
| gcgggacgta acaaccaagg taaattgact gtaagacacc atggtggtgg acacaaacgt | 180 |
| caataccgtg ttatcgattt taaacgtaac aaagatggta tcaatgcaaa agttgattct | 240 |
| attcaatatg atccaaaccg ctcagcaaac atcgctttag ttgtatatgc agacggtgaa | 300 |
| aaacgatata tcattgctcc taaggatta gaagtaggtc aaatcgttga agtggtgct | 360 |
| gaagctgaca tcaaagttgg taacgcatta ccattacaaa acattccagt tggtacagta | 420 |
| gtacacaaca tcgagcttaa acctggtaaa ggtggacaaa tcgctcgttc agctggtgca | 480 |
| agtgctcaag tacttggtaa agaaggtaaa tacgtattaa tcagattaag atctggtgaa | 540 |
| gttcgtatga tcttatctac ttgccgtgct acaatcggtc aagttggtaa cctacaacac | 600 |
| gaattagtta acgttggtaa agccggacgt tcaagatgga aaggtatccg tccaacagtt | 660 |
| cgtggttctg taatgaaccc taacgatcac ccacacggtg gtggtgaagg tcgtgctcct | 720 |
| atcggtagac catctccaat gtcaccatgg ggtaaaccta cgcttggtaa gaaaactcgt | 780 |
| cgtggtaaaa aatcatcaga caaacttatc gttcgtggac gtaagaaaaa ataa | 834 |

<210> SEQ ID NO 81
<211> LENGTH: 180
<212> TYPE: DNA
<213> ORGANISM: Staphylococcus aureus

<400> SEQUENCE: 81

| | | |
|---|---|---|
| atggctaaat acaaattac cctcactcgt agtgttattg gtcgtcctga acacaacgt | 60 |
| aaaactgttg aagctttagg tcttaaaaag actaacagtt cagtagttgt tgaagataac | 120 |
| cctgctattc gtgggcaaat caacaaagtt aagcacttag taacagtaga agaaaaataa | 180 |

<210> SEQ ID NO 82
<211> LENGTH: 174
<212> TYPE: DNA
<213> ORGANISM: Staphylococcus aureus

<400> SEQUENCE: 82

| | | |
|---|---|---|
| atggcagtac caaaaagaag aacttctaaa actagaaaaa acaaacgtcg tacgcatttc | 60 |
| aaaatttcag taccaggtat gactgaatgc ccaaactgtg gcgaatacaa attatcacac | 120 |
| cgtgtatgta aaaactgtgg ttcttacaat ggcgaagaag tagcagctaa ataa | 174 |

<210> SEQ ID NO 83
<211> LENGTH: 138
<212> TYPE: DNA
<213> ORGANISM: Staphylococcus aureus

<400> SEQUENCE: 83

| | | |
|---|---|---|
| atggtaaaac gtacttatca accaaataaa cgtaaacata gtaaagttca tggtttcaga | 60 |
| aaacgcatga gcacaaaaaa tggccgtaaa gttttagcgc gccgtcgtcg taaaggccgt | 120 |
| aaagtttat ctgcataa | 138 |

<210> SEQ ID NO 84
<211> LENGTH: 663
<212> TYPE: DNA
<213> ORGANISM: Staphylococcus aureus

<400> SEQUENCE: 84

```
atgaccaaag gaatcttagg aagaaaaatt gggatgacac aagtattcgg agaaaacggt      60
gaattaatcc ctgtaacagt agtagaagct aaagaaaatg ttgtattaca aaagaaaact     120
gtagaagttg atggatacaa cgcaatccaa gttggatttg aagacaaaaa agcatacaaa     180
aaagatgcaa atctaataa atatgctaat aaaccagctg aaggtcacgc taaaaaagct     240
gacgcagcac ctaagcgctt cattcgtgaa ttccgcaatg tagacgtgga tgcttacgaa     300
gtaggtcaag aagtctcagt agatactttt gtagctggcg acgttattga cgtaacaggc     360
gtatcaaaag gtaaaggttt ccaaggtgca attaaacgcc acggacaatc tcgtggacct     420
atgtcacacg gttctcattt ccacagagca ccaggttctg taggtatggc ttcagatgct     480
tctagagtat ttaaaggcca aaaaatgcca ggacgtatgg gtggaaacac tgtaactgtt     540
caaaacttag aagtagttca agttgacaca gaaaacaaag ttatcttagt aaaaggtaac     600
gtacctggac ctaaaaaagg tttagtagaa atcagaactt caattaaaaa aggtaataaa     660
taa                                                                   663
```

<210> SEQ ID NO 85
<211> LENGTH: 540
<212> TYPE: DNA
<213> ORGANISM: Staphylococcus aureus

<400> SEQUENCE: 85

```
ttgaaccgtt taaagaaaaa gtttaacact gaagttactg aaaacttaat gaaaaaattc      60
aattatagtt cagtaatgga agtaccaaaa atagataaaa tcgttgtgaa catgggtgta     120
ggtgacgcag tacaaaattc taaagtatta gacaatgctg ttgaagaatt agaattgatc     180
actggtcaaa accattagt aactaaagct aaaaaatcaa tcgcgacttt ccgtttacgt     240
gaaggtatgc caatcggtgc gaaagtaaca cttcgcggtg aaagaatgta tgaattctta     300
gacaaattaa tttcagtatc attaccacgt gtacgtgact tccaaggtgt ttctaaaaaa     360
gcatttgacg gacgcggtaa ctacacttta ggtgttaaag aacaattaat ttcccagaa     420
atcgactatg ataaagtaag taaagttaga ggaatggata ttgttatcgt aacgactgct     480
aacactgatg aagaagctcg tgaattgtta gctaacttcg gtatgccatt ccgtaaataa     540
```

<210> SEQ ID NO 86
<211> LENGTH: 537
<212> TYPE: DNA
<213> ORGANISM: Staphylococcus aureus

<400> SEQUENCE: 86

```
atgagtcgtg ttggtaagaa aattattgac atccctagtg acgtaacagt aactttttgat      60
ggaaatcatg taactgttaa aggtcctaaa ggtgaattat caagaacttt aaatgaaaga     120
atgcattca acaagaaga aaacacaatt gaagttgtaa gaccatctga ttctaaagaa     180
gatagaacaa accatggtac aactcgtgct ttattaaaca atatggtaca aggtgtttct     240
caaggatacg taaagtact tgaacttgtt ggtgtaggtt accgtgctca aatgcaaggt     300
aaagacttaa tccttaacgt tggttattct cacccagtag aaattaaagc tgaagaaaac     360
attactttct cagttgagaa aaacacagtc gttaaagttg aaggtatttc aaaagaacaa     420
gttggagcat agcatctaa catccgttca gtaagacctc cagagcctta caaaggtaaa     480
ggtattcgtt accaaggtga aatcgttcgc cgtaaagaag gtaaaactgg taaataa     537
```

<210> SEQ ID NO 87
<211> LENGTH: 369
<212> TYPE: DNA
<213> ORGANISM: Staphylococcus aureus

<400> SEQUENCE: 87

```
atggctaatc atgaacaaat cattgaagcg attaaagaaa tgtcagtatt agaattaaac    60
gacttagtaa aagcaattga agaagaattt ggtgtaactg cagctgctcc agtagcagta   120
gcaggtgcag ctggtggcgc tgacgctgca gcagaaaaaa ctgaatttga cgttgagtta   180
acttcagctg gttcatctaa aatcaaagtt gttaaagctg ttaaagaagc aactggttta   240
ggattaaaag atgctaaaga attagtagac ggagctccta aagtaatcaa agaagcttta   300
cctaaagaag aagctgaaaa acttaaagaa caattagaag aagttggagc tactgtagaa   360
ttaaaataa                                                           369
```

<210> SEQ ID NO 88
<211> LENGTH: 390
<212> TYPE: DNA
<213> ORGANISM: Staphylococcus aureus

<400> SEQUENCE: 88

```
atggcacgta aacaagtatc tcgtaaacgt agagtgaaaa agaatattga aaatggtgta    60
gcacacatcc gttcaacatt caacaacact attgtaacta tcactgatga gttcggtaat   120
gctttatcat ggtcatcagc tggtgcatta ggattcaaag gatctaaaaa atcaacacca   180
tttgcagcac aaatggcttc tgaaactgca tctaaatcag ctatggagca tggttttaaaa  240
acagttgaag taacagttaa aggacctggt ccaggtcgtg aatcagctat tcgtgcatta   300
caatctgcag gtttagaagt aactgcgatc agagacgtta ctccagtacc tcataacggt   360
tgtcgtccac caaaacgtcg tcgtgtataa                                    390
```

<210> SEQ ID NO 89
<211> LENGTH: 414
<212> TYPE: DNA
<213> ORGANISM: Staphylococcus aureus

<400> SEQUENCE: 89

```
atgccaacta ttaaccaatt agtacgtaaa ccaagacaaa gcaaaatcaa aaaatcagat    60
tctccagctt taaataaagg tttcaacagt aaaaagaaaa aatttactga cttaaactca   120
ccacaaaaac gtggtgtatg tactcgtgta ggtacaatga cacctaaaaa acctaactca   180
gcgttacgta aatatgcacg tgtgcgttta tcaaacaaca tcgaaattaa cgcatacatc   240
cctggtatcg acataaactt acaagaacac agtgttgtac ttgtacgtgg tggacgtgta   300
aaagacttac caggtgtgcg ttaccatatt gtacgtggag cacttgatac ttcaggtgtt   360
gacggacgta gacaaggtcg ttcattatac ggaactaaga aacctaaaaa ctaa         414
```

<210> SEQ ID NO 90
<211> LENGTH: 366
<212> TYPE: DNA
<213> ORGANISM: Staphylococcus aureus

<400> SEQUENCE: 90

```
atggcacgta ttgcaggagt agatattcca cgtgaaaaac gcgtagttat ctcattaact    60
tatatatacg gtatcggtac gtcaactgct caaaaaattc ttgaagaagc taacgtatca   120
gctgatactc gtgtgaaaga tttaactgat gacgaattag gtcgcatccg tgaagttata   180
```

```
gacggttata aagtcgaagg tgacttacgt cgtgaaacta acttaaatat caaacgttta    240
atggaaattt catcataccg tggtatccgt caccgtcgtg gtttaccagt tcgtggtcaa    300
aaaacgaaaa acaacgcgcg tactcgtaaa ggaccagtta aacggtagc taacaagaaa    360 aaataa                                                              366
```

<210> SEQ ID NO 91
<211> LENGTH: 186
<212> TYPE: DNA
<213> ORGANISM: Staphylococcus aureus

<400> SEQUENCE: 91

```
gtggctaaaa cttcaatggt tgctaagcaa caaaaaaaac aaaaatatgc agttcgtgaa     60
tacactcgtt gtgaacgttg tggccgtcca cattctgtat atcgtaaatt taaattatgc    120
cgtatttgtt ccgtgaatt agcttacaaa ggccaaatcc ctggcgttcg taaagctagc    180
tggtaa                                                              186
```

<210> SEQ ID NO 92
<211> LENGTH: 270
<212> TYPE: DNA
<213> ORGANISM: Staphylococcus aureus

<400> SEQUENCE: 92

```
atggcaattt cacaagaacg taaaaacgaa atcattaaag aataccgtgt acacgaaact     60
gatactggtt caccagaagt acaaatcgct gtacttactg cagaaatcaa cgcagtaaac    120
gaacacttac gtacacacaa aaaagaccac cattcacgtc gtggattatt aaaaatggta    180
ggtcgtcgta gacatttatt aaactactta cgtagtaaag atattcaacg ttaccgtgaa    240
ttaattaaat cacttggtat ccgtcgttaa                                    270
```

<210> SEQ ID NO 93
<211> LENGTH: 264
<212> TYPE: DNA
<213> ORGANISM: Staphylococcus aureus

<400> SEQUENCE: 93

```
gtgagcgaaa gaaacgatcg taaagtttat gtaggtaaag ttgtttcaga caaaatggac     60
aagactatta cagtacttgt tgaaacttac aaaacacaca attatacgg taaacgagta    120 aaatactcta aaaatacaa aactcatgat gaaaacaatt cagctaaatt aggagacatt    180
gttaaaattc aagaaactcg tcctttatca gcaacaaaac gttttcgtat agtagagatt    240
gttgaagagt cagtaattat ttaa                                          264
```

<210> SEQ ID NO 94
<211> LENGTH: 279
<212> TYPE: DNA
<213> ORGANISM: Staphylococcus aureus

<400> SEQUENCE: 94

```
atggctcgta gtattaaaaa aggacctttc gtcgatgagc atttaatgaa aaaagttgaa     60
gctcaagaag gaagcgaaaa gaaacaagta atcaaaacat ggtcacgtcg ttctacaatt    120
ttccctaatt tcatcggaca tacttttgca gtatacgacg acgtaaaaca cgtacctgta    180
tatgtaactg aagatatggt aggtcataaa ttaggtgagt tgctcctac tcgtacattc    240 aaaggacacg ttgcagacga caagaaaaca agaagataa                          279
```

<210> SEQ ID NO 95
<211> LENGTH: 177
<212> TYPE: DNA
<213> ORGANISM: Staphylococcus aureus

<400> SEQUENCE: 95

| | | |
|---|---|---|
| atgtctaaaa cagtagtacg taaaaatgaa tcacttgaag atgcgttacg tagatttaaa | 60 |
| cgttcagttt ctaaaagtgg aacaatccaa gaagtacgta aacgtgaatt ttacgaaaaa | 120 |
| ccaagcgtaa aacgtaaaaa gaaatcagaa gctgcacgta acgtaaaatt caaataa | 177 |

<210> SEQ ID NO 96
<211> LENGTH: 654
<212> TYPE: DNA
<213> ORGANISM: Staphylococcus aureus

<400> SEQUENCE: 96

| | | |
|---|---|---|
| gtgggtcaaa aaattaatcc aatcggactt cgtgttggta ttatccgtga ttgggaagct | 60 |
| aaatggtatg ctgaaaaaga cttcgcttca cttttacacg aagatttaaa aatccgtaaa | 120 |
| tttattgata tgaattaaa agaagcatca gtttctcacg tagagattga acgtgctgca | 180 |
| aaccgtatca acattgcaat tcatactggt aaacctggta tggtaattgg aaaggcggt | 240 |
| tcagaaatcg aaaaattacg caacaaatta atgcgttaa ctgataaaaa agtacacatc | 300 |
| aacgtaattg aaatcaaaaa agttgatctt gacgctcgtt tagtagctga aaacatcgca | 360 |
| cgtcaattag aaaaccgtgc ttcattccgt cgtgtacaaa acaagcaat cactagagct | 420 |
| atgaaacttg tgctaaagg tatcaaaact caagtatctg gtcgtttagg cggagctgac | 480 |
| atcgctcgtg ctgaacaata ttcagaagga actgttccac ttcatacgtt acgtgctgac | 540 |
| atcgattatg cacacgctga agctgacact acttacggta aattaggcgt taaagtatgg | 600 |
| atctatcgtg gagaagttct tcctactaag aacactagtg gaggaggaaa ataa | 654 |

<210> SEQ ID NO 97
<211> LENGTH: 603
<212> TYPE: DNA
<213> ORGANISM: Staphylococcus aureus

<400> SEQUENCE: 97

| | | |
|---|---|---|
| atggctcgat tcagaggttc aaactggaaa aaatctcgtc gtttaggtat ctctttaagc | 60 |
| ggtactggta agaattaga aaaacgtcct tacgcaccag acaacatgg tccaaaccaa | 120 |
| cgtaaaaaat tatcagaata tggtttacaa ttacgtgaaa acaaaaatt acgttactta | 180 |
| tatggaatga ctgaaagaca attccgtaac acatttgaca tcgctggtaa aaaattcggt | 240 |
| gtacacggtg aaaacttcat gatttttatta gcaagtcgtt tagacgctgt tgtttattca | 300 |
| ttaggtttag ctcgtactcg tcgtcaagca cgtcaattag ttaaccacgg tcatatctta | 360 |
| gtagatggta acgtgttga tattccatct tattctgtta aacctggtca acaatttca | 420 |
| gttcgtgaaa atctcaaaaa attaaacatc atcgttgaat cagttgaaat caacaatttc | 480 |
| gtacctgagt acttaaactt tgatgctgac agcttaactg gtactttcgt acgtttacca | 540 |
| gaacgtagcg aattacctgc tgaaattaac gaacaattaa tcgttgagta ctactcaaga | 600 |
| taa | 603 |

<210> SEQ ID NO 98
<211> LENGTH: 501
<212> TYPE: DNA
<213> ORGANISM: Staphylococcus aureus

<400> SEQUENCE: 98

```
atggctcgta gagaagaaga gacgaaagaa tttgaagaac gcgttgttac aatcaaccgt      60
gtagcaaaag ttgtaaaagg tggtcgtcgt ttccgtttca ctgcattagt tgtagttgga     120
gacaaaaatg gtcgtgtagg tttcggtact ggtaaagctc aagaggtacc agaagcaatc     180
aaaaaagctg ttgaagcagc taaaaaagat ttagtagttg ttccacgtgt tgaaggtaca     240
actccacaca caattactgg ccgttacggt tcaggaagcg tatttatgaa accggctgca     300
cctggtacag gagttatcgc tggtggtcct gttcgtgccg tacttgaatt agcaggtatc     360
actgatatct taagtaaatc attaggatca aacacaccaa tcaacatggt tcgtgctaca     420
atcgatggtt tacaaaacct taaaaatgct gaagatgttg cgaaattacg tggcaaaaca     480
gtagaagaat tatacaatta a                                               501
```

<210> SEQ ID NO 99
<211> LENGTH: 297
<212> TYPE: DNA
<213> ORGANISM: Staphylococcus aureus

<400> SEQUENCE: 99

```
atgagaacat atgaagttat gtacatcgta cgcccaaaca ttgaggaaga tgctaaaaaa      60
gcgttagttg aacgtttcaa cggtatctta gctactgaag gtgcagaagt tttagaagca     120
aaagactggg gtaaacgtcg cctagcttat gaaatcaatg atttcaaaga tggcttctac     180
aacatcgtac gtgttaaatc tgataacaac aaagctactg acgaattcca acgtctagct     240
aaaatcagtg acgatatcat tcgttacatg gttattcgtg aagacgaaga caagtaa        297
```

<210> SEQ ID NO 100
<211> LENGTH: 471
<212> TYPE: DNA
<213> ORGANISM: Staphylococcus aureus

<400> SEQUENCE: 100

```
atgcctcgta aaggatcagt acctaaaaga gacgtattac cagatccaat tcataactct      60
aagttagtaa ctaaattaat taacaaaatt atgttagatg gtaaacgtgg aacagcacaa     120
agaattcttt attcagcatt cgacctagtt gaacaacgca gtggtcgtga tgcattagaa     180
gtattcgaag aagcaatcaa caacattatg ccagtattag aagttaaagc tcgtcgtgta     240
ggtggttcta actatcaagt accagtagaa gttcgtccag agcgtcgtac tactttaggt     300
ttacgttggt tagttaacta tgcacgtctt cgtggtgaaa aaacgatgga agatcgttta     360
gctaacgaaa ttttagatgc agcaaataat acaggtggtg ccgttaagaa acgtgaggac     420
actcacaaaa tggctgaagc aaacaaagca tttgctcact accgttggta a              471
```

<210> SEQ ID NO 101
<211> LENGTH: 321
<212> TYPE: DNA
<213> ORGANISM: Staphylococcus aureus

<400> SEQUENCE: 101

```
atgattactg ttgatattac agttaatgat gaaggcaaag taacagacgt tattatggat      60
ggccatgctg accatggtga atatggtcat gatatcgttt gtgctggagc ttcagctgta     120
ttgtttggta gtgttaatgc gattatagga ttgacatctg agagaccaga tatcaattat     180
gacgacaatg gtggtcattt tcatataaga agcgttgata caaacaacga tgaagcgcaa     240
```

```
ctaattcttc aaacaatgct tgtgtcttta caaactattg aagaagaata taatgagaat      300
attagattaa attataagtg a                                               321
```

US 9,909,123 B2

ANTISENSE MOLECULES FOR TREATMENT OF *STAPHYLOCOCCUS AUREUS* INFECTION

GOVERNMENT INTEREST

This work is based in part by the Defense Advanced Research Project Agency under Phase I SBIR contract number W911QX-12-C-0072. The US government has certain rights to the invention.

REFERENCE TO SEQUENCE LISTING SUBMITTED ELECTRONICALLY VIA EFS-WEB

The content of the electronically submitted sequence listing (File Name: 3344_0030001_SL_UpdatedFEB.txt; Size: 36,298 bytes; and Date of Creation: Feb. 11, 2016) was originally submitted in the International Application No. PCT/US2014/028830 and is incorporated herein by reference in its entirety.

FIELD OF THE INVENTION

The field of the invention relates to antisense polynucleotide reagents targeting ribosomal protein expression and useful for treatment of *Staphylococcus aureus* infection.

SUMMARY OF THE INVENTION

Provided are antisense molecules useful for treatment of *Staphylococcus aureus* infection and the inhibition of *Staphylococcus aureus* growth. The antisense molecules target *Staphylococcus aureus* ribosomal proteins and may comprise natural nucleic acid polymers and non-natural nucleic acid polymers. Non-natural nucleic acid polymers include polymers with modified backbones, such as PNA, PMO, and synthetically-modified DNA and RNA. The invention includes any type of synthetically-modified DNA or RNA that hybridizes to natural DNA and RNA. In one embodiment, the antisense molecules are in the form of a salt or a complex. In one embodiment, the antisense molecule is complexed to a cationic polymeric molecule. In another embodiment, the antisense molecule is conjugated to a cell penetrating molecule. Also provided are pharmaceutical compositions comprising the antisense molecules of the invention.

In one embodiment the invention provides an antisense molecule or salt thereof that inhibits the growth of *Staphylococcus aureus* comprising a polynucleotide sequence that is antisense to the coding region of a *Staphylococcus aureus* ribosomal protein and hybridizes to said coding region under physiological conditions. In one embodiment, the antisense molecule is 10 to 50 nucleobases in length. In another embodiment, the antisense, molecule is fully complementary to a coding region of a *staphylococcus aureus* ribosomal protein. In another embodiment, the antisense molecule is at least 80% identical to a sequence selected from the group consisting of SEQ ID NOS: 1-50. In another embodiment, the antisense molecule is an oligonucleotide. In another embodiment, the antisense molecule is substantially pure. In another embodiment, the antisense molecule comprises a modified backbone. In another embodiment, the modified backbone is a PNA backbone. In another embodiment, the antisense molecule inhibits expression of LSU ribosomal protein L15p (L27Ae) or SSU ribosomal protein S17p (S11e). In another embodiment, the antisense molecule is conjugated to a cell penetration molecule. In another embodiment, the cell penetration molecule is a peptide. In another embodiment, the peptide is a cell-penetrating peptide (CPP). In another embodiment, the antisense molecule is complexed to a delivery polymer. In another embodiment, the delivery polymer is a cationic block copolymer comprising phosphonium or ammonium ionic groups.

The invention also provides a method of inhibiting the growth of *Staphylococcus aureus*, comprising administering an effective amount of an antisense molecule or composition of the invention to a tissue containing said *Staphylococcus aureus* or suspected of containing *Staphylococcus aureus*. In one embodiment, the administering is topical administration.

The invention also provides a method of treating *Staphylococcus aureus* infection, comprising administering to an animal in need thereof an effective amount of the antisense molecule or composition of the invention.

BRIEF DESCRIPTION OF THE SEQUENCE LISTING

Figure 1:
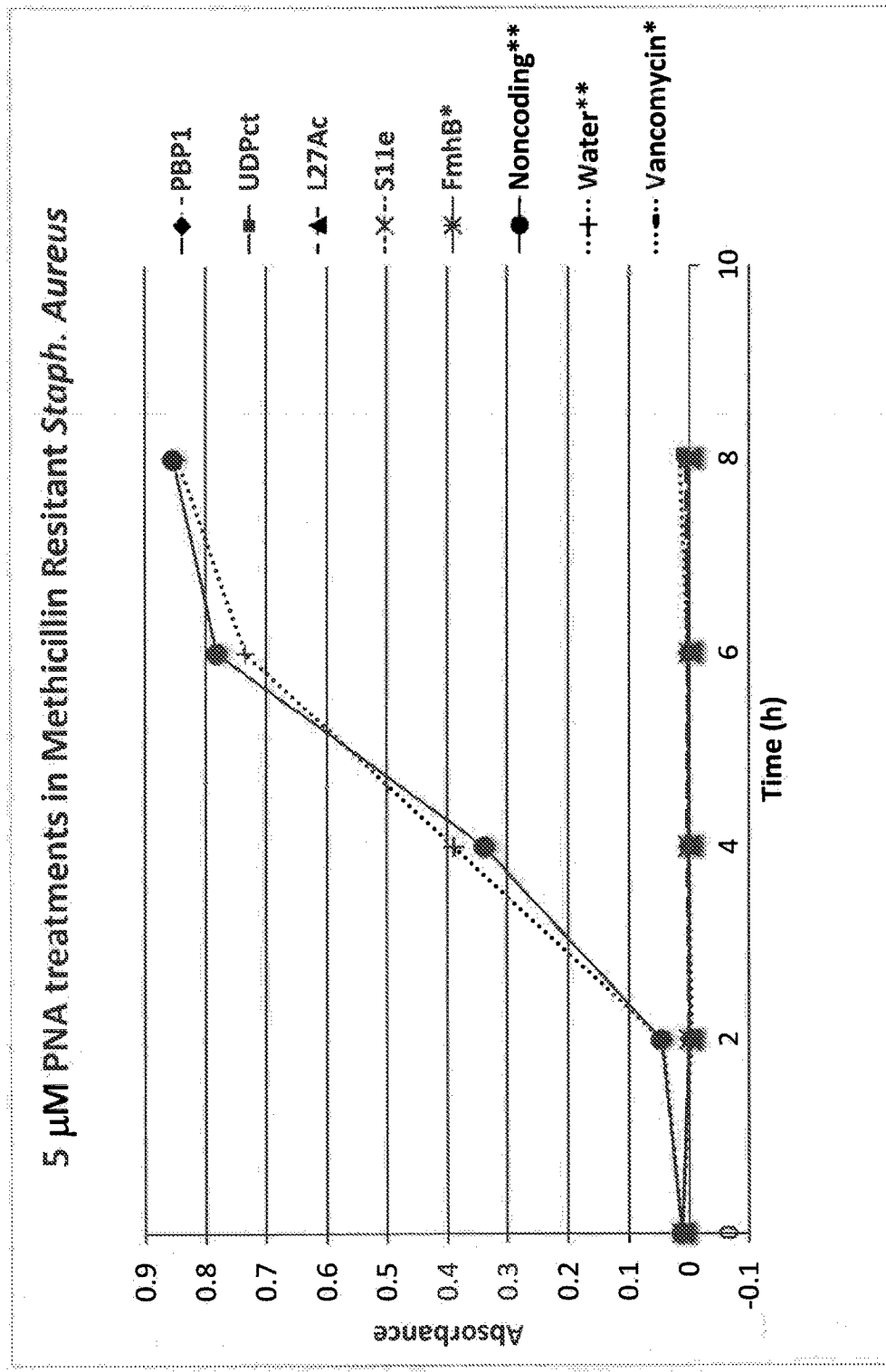
FIG. 1. MRSA in vitro studies. Efficacy of antibacterial nucleic acid agents is demonstrated. Peptide-PNA was tested against bacteria in culture of MRSA USA 300. Vancomycin was used to standardize these results for additional studies.

The polynucleotide sequences in the sequence listing include the coding sequences for *Staphylococcus aureus* ribosomal proteins. See, SEQ ID NOS: 65-101.

The polynucleotide sequences in the sequence listing also include antisense deoxyribonucleic acids (DNA) and/or modified nucleic acids, such as peptide nucleic acids (PNA). These sequences are capable of knockdown of expression of at least the following *Staphylococcus aureus* ribosomal protein as set forth in Table 1:

TABLE 1

Antisense Polynucleotides Targeting Ribosomal Proteins

| Protein Target | Antisense Polynucleotide Sequence |
|---|---|
| LSU ribosomal protein L10p (P0) | AGACATTCAGACACC (SEQ ID NO: 21) |
| LSU ribosomal protein L11p (L12e) | TAGCCACGATGTGCA (SEQ ID NO: 19) |
| LSU ribosomal protein L13p (L13Ae) | ACGCATAATAAT (SEQ ID NO: 8) |
| LSU ribosomal protein L13p (L13Ae) | TTGACGCATAATAAT (SEQ ID NO: 33) |

TABLE 1-continued

Antisense Polynucleotides Targeting Ribosomal Proteins

| Protein Target | Antisense Polynucleotide Sequence |
|---|---|
| LSU ribosomal protein L14p (L23e) | GTTGGATCATTA (SEQ ID NO: 13) |
| LSU ribosomal protein L14p (L23e) | TGGATCATTAGTTAA (SEQ ID NO: 42) |
| LSU ribosomal protein L15p (L27Ae) | TTTCATTTCGGCACC (SEQ ID NO: 1) |
| LSU ribosomal protein L16p (L10e) | GGTAGTAACATTATT (SEQ ID NO: 43) |
| LSU ribosomal protein L18p (L5e) | GATCATTTCAATACT (SEQ ID NO: 38) |
| LSU ribosomal protein L19p | TGATTTGTCATTATA (SEQ ID NO: 25) |
| LSO ribosomal protein L1p (L10Ae) | TTAGCCATTTATAGT (SEQ ID NO: 20) |
| LSU ribosomal protein L20p | ACTCGTGGCATA (SEQ ID NO: 6) |
| LSU ribosomal protein L21p | AGCAAACATACTTTG (SEQ ID NO: 31) |
| LSU ribosomal protein L22p (L17e) | TTCCATTAGGATGTC (SEQ ID NO: 45) |
| LSU ribosomal protein L23p (L23Ae) | TTCCATTATCCGAGC (SEQ ID NO: 48) |
| LSU ribosomal protein L27p | AACATCGGAATG (SEQ ID NO: 5) |
| LSU ribosomal protein L27p | TAACATCGGAATGCA (SEQ ID NO: 29) |
| LSU ribosomal protein L28p | TGTTTACCCATA (SEQ ID NO: 4) |
| LSU ribosomal protein L2p (L8e) | TAGCCATTGTCG (SEQ ID NO: 16) |
| LSU ribosomal protein L2p (L8e) | AGCCATTGTCGCTTA (SEQ ID NO: 47) |
| LSU ribosomal protein L30p (L7e) | TTTAGCCATAACTAG (SEQ ID NO: 36) |
| LSU ribosomal protein L32p | TACTGCCATGATATA (SEQ ID NO: 24) |
| LSU ribosomal protein L34p | GTFTTACCATGCAAA (SEQ ID NO: 50) |
| LSU ribosomal protein L3p (L3e) | CATCGAAAGTCC (SEQ ID NO: 17) |
| LSU ribosomal protein L3p (L3e) | GGTCATCGAAAGTCC (SEQ ID NO: 49) |
| LSU ribosomal protein L5p (L11e) | CGGTTCAAAGTGGGA (SEQ ID NO: 41) |
| LSU ribosomal protein L6p (L9e) | TCATGTTATGGC (SEQ ID NO: 12) |
| LSU ribosomal protein L6p (L9e) | ACTCATGTTATGGCA (SEQ ID NO: 39) |
| ribosomal protein L7Ae family protein | TATACTCATTTTGGG (SEQ ID NO: 26) |
| SSU ribosomal protein S11p (S14e) | TTACGTGCCATT (SEQ ID NO: 9) |
| SSU ribosomal protein S11p (S14e) | TTTACGTGCCATTTA (SEQ ID NO: 34) |
| SSU ribosomal protein S12p (S23e) | GTTGGCATGTGATAT (SEQ ID NO: 22) |
| SSU ribosomal protein S13p (S18e) | TACGTGCCATAT (SEQ ID NO: 10) |
| SSU ribosomal protein S13p (S18e) | TACGTGCCATATTAA (SEQ ID NO: 35) |
| SSU ribosomal protein S14p (S29e) Zinc-dependent | TTTAGCCACTTAATT (SEQ ID NO: 40) |
| SSU ribosomal protein S15p (S13e) | AAATTGCCATAATCA (SEQ ID NO: 27) |
| SSU ribosomal protein S17p (S11e) | TCTTTCGCTCAC (SEQ ID NO: 14) |
| SSU ribosomal protein S17p (511e) | CGCTCACTTTTGTAA (SEQ ID NO: 2) |
| SSU ribosomal protein S19p (S15e) | TACGAGCCATTT (SEQ ID NO: 15) |
| SSU ribosomal protein S19p (S15e) | GAGCCATTTGGGCGC (SEQ ID NO: 46) |
| SSU ribosomal protein S21p | TTTAGACATCTGTAT (SEQ ID NO: 28) |
| SSU ribosomal protein S3p (S3e) | TTGACCCACAGTATT (SEQ ID NO: 44) |
| SSU ribosomal protein S4p (S9e) | CGAGCCATAATA (SEQ ID NO: 7) |
| SSU ribosomal protein S4p (S9e) | GAGCCATAATAAGAC (SEQ ID NO: 32) |
| SSU ribosomal protein S5p (S2e) | CGAGCCATGTAT (SEQ ID NO: 11) |
| SSU ribosomal protein S5p (S2e) | CGAGCCATGTATTTG (SEQ ID NO: 37) |
| SSU ribosomal protein S6p | GTTCTCATTTTATAT (SEQ ID NO: 18) |
| SSU ribosomal protein S7p (S5e) | ACGAGGCATAAT (SEQ ID NO: 3) |
| SSU ribosomal protein S7p (S5e) | TTTACGAGGCATAAT (SEQ ID NO: 23) |
| Potential ribosomal protein | CAGTAATCATAATAA (SEQ ID NO: 30) |

The sequence listing also contains control sequences of tRNA-dependent lipid II glycine ligase (FmhB): ttttccatgatt-tat (SEQ ID NO 62), and Noncoding negative control (NC): aacattttggtttt (SEQ ID NO 63).

The peptide sequences in the sequence listing include peptides that target and/or localize nucleic acids and nanoparticles to bacterial cells and promote bacterial membrane permeation. See Table 2:

TABLE 2

Cell Penetrating Peptides

| Peptide Name | Amino Acid Sequence |
|---|---|
| KFF peptide | KFFKFFKFFK (SEQ ID NO: 51) |
| RFF peptide | RFFRFFRFFR (SEQ ID NO: 52) |
| Magainin 2 | GIGKWLHSAKKFGKAFVGEIMNS (SEQ ID NO: 53) |
| Transportin 10 | AGYLLGKINLKALAALAKKIL (SEQ ID NO: 54) |
| Indolicidin | ILPWKWPWWPWRR (SEQ ID NO: 61) |
| TAT peptide | GRKKRRQRRRPQ (SEQ ID NO: 60) |
| PENETRATIN 1 peptide | RQIKIWFQNRRMKWKK (SEQ ID NO: 59) |
| amphipathic peptide | LLIILRRRIRKQAHAHSK (SEQ ID NO: 58) |
| cyclic d,1-alpha-peptide | KQRWLWLW (SEQ ID NO: 57) |
| cyclic d,1-alpha-peptide | RRKWLWLW (SEQ ID NO: 56) |
| cyclic d,1-alpha-peptide | KKLWLW (SEQ ID NO: 55) |

Definitions

The terms used in this disclosure have ordinary meanings as used in the art.

A polymer is a linear chain of units called monomers. In a polymer, the monomeric units may be identical or they may be different. Polymers may be natural (made in nature) or may be synthetic. Polymers of the present invention comprise nucleic acid polymers, polypeptides, and synthetic delivery polymers.

A nucleic acid is a linear polymer of nucleotides. Nucleic acids made in nature contain deoxyribonucleotide (DNA) bases adenine, cytosine, guanine, and thymine; or ribonucleotide (RNA) bases adenine, cytosine, guanine, and uracil. As used herein, polynucleotide and oligonucleotide refer to a nucleic acid molecule and include genomic DNA, cDNA, RNA, or mRNA of any length. Nucleic acid, polynucleotide, oligonucleotide are terms that may be used interchangeably.

Modified nucleic acids are non-natural polymers that hybridize to natural DNA and RNA with sequence specificity according to Watson-Crick base paring rules. Examples of modified nucleic acids are phosphorothioate-oligodeoxynucleotides (PS-ODNs), locked nucleic acids (LNAs), 2'-O-methyloligoribonucleotides (2'O-Mes), phosphorodiamidate morpholino oligonucleotides (PMOs), and peptide nucleic acids (PNAs). Modified nucleic acids have modified backbones and are generally more resistant to degradation than natural nucleic acids. The invention includes any type of synthetically-modified DNA or RNA that hybridizes to natural DNA and RNA. See, e.g., U.S. Pat. Nos. 5,116,195, 5,539,082, 5,527,675, 5,623,049, 5,714,331, 5,736,336, 5,773,571, 5,786,461, 5,811,232, 5,837,459, 5,874,564, 5,891,625, 5,972,610, 5,986,053, 6,107,470, 6,174,870, 7,098,192, 7,696,345, 8,124,745, 8,354,093, 8,357,664, Wagner et al., *Nucl. Acid Res.* 19:5965-71 (1991); and Koshkin et al., *Tetrahedron* 54:3607-30 (1998).

Antisense molecules of the invention may also be composed of non-natural polymers that hybridize to natural nucleic acids. Atypical nucleoside bases may also be employed, such as methylated bases, phosphorylated bases, inosine, thiouridine, pseudouridine, dihydrouridine, queuosine, and wyosine, among others. Examples of such antisense polymers comprising atypical bases are disclosed in U.S. Pat. Nos. 7,875,733, 7,919,612, 7,939,677, 8,314,229, 8,372,969, and 8,377,898.

The term antisense polynucleotide refers to a nucleic acid molecule that is complementary to at least a portion of a target nucleotide sequence of interest and hybridizes to the target nucleotide sequence under physiological conditions. Antisense molecules specifically hybridize with one or more nucleic acids encoding a preselected target nucleic acid. The terms target nucleic acid and nucleic acid encoding the target encompass DNA encoding the target, RNA (including pre-mRNA and mRNA) transcribed from such DNA, and also cDNA derived from such RNA. The hybridization of an antisense compound with its target nucleic acid interferes with the normal function of the nucleic acid. This modulation of function of a target nucleic acid by compounds which specifically hybridize to it is generally referred to as antisense. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the target. In the context of the present invention, modulation means either an increase (stimulation) or a decrease (inhibition) in the expression of a gene. In the context of the present invention, inhibition is the form of modulation of gene expression.

Polynucleotides are described as complementary to one another when hybridization occurs in an antiparallel configuration between two single-stranded polynucleotides.

The percent identity between the two sequences is a function of the number of identical positions shared by the sequences, taking into account the number of gaps, mid the length of each gap, which need to be introduced for optimal alignment of the two sequences. The comparison of sequences and determination of percent identity and similarity between two sequences can be accomplished using a mathematical algorithm (see e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two sequences is determined based on alignments generated with the Clustal W algorithm (Thompson, J. D. et al., 1994, *Nucleic acids Res.* 22:4673-4680). This algorithm is incorporated into many commercial software packages, in this case the alignX software program in the Vector NTI suite (version 8.0). Default Clustal W parameters were used to generate pairwise alignments from which percent identity values were calculated (gap opening penalty of 10; gap extension penalty of 0.1). The percent identity is defined as the number of identical bases divided by the total number of bases and multiplied by 100. If sequences in the alignment are of different lengths (due to gaps or extensions), the length of the longest sequence will be used in the calculation, representing the value for total length.

Proteins are polymers containing one or more chains of amino acids bonded together by peptide bonds. Proteins typically fold into a three dimensional form, facilitating a biological function.

A polypeptide is a polymer of amino acids bonded together by peptide bonds. The terms protein and polypeptide and peptide are generally used interchangeably, although polypeptides and peptides are generally shorter in length than proteins.

The terms charged, uncharged, cationic and anionic refer to the predominant state of a chemical moiety at near-neutral pH, e.g. about 6 to 8. In one embodiment, the term refers to the predominant state of the chemical moiety at physiological pH, that is, about 7.4. Thus, a cationic backbone linkage is predominantly positively charged at pH 7.4.

The term substantially pure means that the antisense molecule is substantially free from other materials such as other nucleic acids, proteins, lipids, carbohydrates, and other materials with which it may be naturally associated. In one embodiment, substantially pure antisense molecules are 95-95% homogeneous by HPLC. In another embodiment, substantially pure antisense molecules are 99-100% homogenous by HPLC.

DETAILED DESCRIPTION OF THE INVENTION

The present invention may be understood by reference to the following detailed description of the embodiments of the invention and examples included herein. The terminology used herein is for the purpose of describing embodiments of the invention and is not intended to be limiting.

Specific aspects of the invention include antisense molecules that are useful for the treatment of *Staphylococcus aureus* infection and/or inhibit the growth of *Staphylococcus aureus* comprising an antisense molecule that is antisense to a *Staphylococcus aureus* ribosomal protein coding region under physiological conditions. In one embodiment, the antisense molecule hybridizes to a *Staphylococcal aureus* ribosomal coding region selected from the group consisting of SEQ ID NOS: 65-101. In one embodiment, the antisense molecule contains 10-50 nucleobases, i.e., is a 10-50-mer. In another embodiment, the antisense molecule is a 10-25-mer, a 12-20-mer, a 12-15-mer, a 11-mer, a 12-mer, a 13-mer, a 14-mer, a 15-mer, a 16-mer, a 17-mer, an 18-mer, a 19-mer, a 20-mer, a 21-mer, a 22-mer, a 23-mer, a 24-mer, a 25-mer, a 26-mer, a 27-mer, a 28-mer, a 29-mer, or a 30-mer. The nucleotide sequence for the antisense molecule is chosen at a binding location that preferably spans the start codon. Proprietary software scans window sizes 10 bases, 11 bases, 12 bases, 13 bases, 14 bases, 15 bases, 16 bases, 17 bases, 18 bases, 19 bases, and/or 20-40 bases (as a non-limiting example) including the start codon and ranks self-folding potential by base content. The software algorithm may be programmed to span the start codon. Alternatively, the algorithm may be programmed to optionally span the start codon region. Selection of antisense sequence can be finalized manually from these data or through an automated process derived from empirical data and parameter weighting. These antisense molecules against ribosomally-expressed genes are substantially orthogonal to the human transcriptome. In one embodiment, the antisense molecules have base lengths exhibiting features such as Tin greater than 37° C., low self-folding, and significant start codon overlap.

In another embodiment, the invention, provides a polynucleotide sequence at least 80% identical to a sequence selected from SEQ ID NO: 1-50. Specifically, the sequences may contain one or more substitutions, additions, deletions, and/or insertions with natural or non-natural nucleotides, such that the target gene modulation activity is not substantially diminished. Variants exhibit at least about 80%, 81%, 82%, 83%, 84% 85%, 86%, 87%, 88%, or 89% sequence identity; and another embodiment at least about 90%, 91%, 92%, 93%, 94%, 95%, 96%, 97%, 98%, or 99% identity to a sequence selected from the group consisting of SEQ ID NOS: 1-50. The percent identity may be readily determined by comparing sequences of the polynucleotides to the corresponding portion of the target polynucleotide, using any method including using computer algorithms well known to those of ordinary skill in the art. Algorithms include the Align or the BLAST algorithm (Altschul, 1991 J. Mol. Biol. 219:555-565; Henikoff and Henikoff, 1992, *Proc. Natl. Acad. Sci. USA* 89:10915-10919).

In one embodiment of the invention, the active ingredient is coupled to a targeting/cell penetration molecule. In one aspect of the invention, the targeting molecule comprises a peptide. The peptide may comprise a cell penetration peptide (CPP). Peptides utilized may have one or more functions to facilitate cell targeting and/or membrane permeation. In particular, the therapeutic polynucleotides of the invention can be delivered to *Staphylococcus aureus* in a host by conjugating peptides to the antisense molecule. The ability to conjugate antisense molecules to peptides for membrane disruption of bacteria provides specificity and reduces toxicity. Examples of cell penetration peptides include those having SEQ ID NOS: 51-61. Additional examples cell penetration peptides and methods to link them to antisense molecules are described in U.S. Pat. Nos. 8,354,387, 8,354,093, 8,313,778, 8,299,236, 8,242,081, 8,211,468, 8,207,293, 8,138,383, 8,044,019, 8,039,587, 7,943,581, and 7,879,813. In another embodiment, the cell penetrating, peptides is derived from HIV tat, herpes virus VP22, the Drosphila Antennapedia homeobox gene product, signal sequences, fusion sequences or protegrin I as disclosed in U.S. Pat. No. 8,338,366. The antisense molecule-peptide conjugate may be prepared by methods of solid-phase synthesis, where cysteine serves as the linker between peptide and DNA. Other methodologies known in the art may be used (See for example, Dirksen, A., et al., *J. Am. Chem. Soc.* 2006. 128, 15602-3).

CPPs useful in the invention are peptides of diverse origins. Cationic nucleic acid carrier peptides form productive nanoparticles when mixed with the synthetic polymers of the invention. One example is the peptide KFFKFFKFFK (SEQ ID NO 51) described in Xie et al., *Molecular Therapy* 2004, 10, 652-659. Additional peptides may include TAT peptide and PENETRATIN. The TAT peptide, GRK-KRRQRRRPQ (SEQ ID NO 60), is derived from the trans-activator of transcription (TAT) of human immunodeficiency virus and is a CPP. CPPs overcome the lipophilic barrier of cell membranes and deliver large molecules and particles inside the cell for their biological actions. PENETRATIN peptide is a 16-amino acid peptide of sequence RQIKIW-FQNRRMKWKK (SEQ ID NO 59) corresponding to the third helix of the homeodomain of Antennapedia protein.

Useful CPPs also encompass cyclic d,1-αpeptides, such as, KQRWLWLW (SEQ ID NO 57), RRKWLWLW (SEQ ID NO 56), and KKLWLW, (SEQ ID NO 55) as described in Fernandez-Lopez et al., Nature 2001, 412, 452-455. These peptides have antibiotic properties of their own, and also function as carriers of cargo for internal cellular delivery. Additionally, amphipathic peptides LLIILRRRIRKQA-HAHSK (SEQ ID NO 58) and transportin 10 (TP10), AGYLLGKINLKALAALAKKIL (SEQ ID NO 54), described in Nekhotiaeva et al. *FASEB J.* 2010, 394-396, form productive nanoparticles. Tryptophan rich peptides, such as Magainin 2 peptide, GIGKWLHSAKKFGKAF-VGEIMNS (SEQ ID NO 53), which was isolated from the African clawed frog (Karas et al, *Biochemistry* 2002, 41, 10723-31), are additional CPPs useful in the present invention. Furthermore, Indolicidin, ILPWKWPWWPWRR (SEQ ID NO: 61), which was isolated from bovine neutrophils, is another CPP useful in the present invention. These and other peptides of similar sequence and properties are recognized by one of skill in the art as functional alternatives and are encompassed by the present invention. Furthermore, these peptides may be modified to improve function as desired or needed.

Bulk peptide and polynucleotide synthesis can be carried out by contract manufacturers, such as Neo Group, Inc. (Cambridge, Mass.) using standard methodologies including solid-scaffold protection/deprotection synthesis via high fidelity synthesizers. The peptide-PNA or peptide-DNA component is the therapeutic molecule which enters the pathogen and disrupts its genetic regulation.

In one embodiment, an antisense molecule is conjugated to a CPP using well known conjugation methods that employ succinimidyl-6-hydrazinonicotinateacetonehydrazone to succinimidyl-4-formylbenzoate coupling, chemistry. This is a specific, well-behaved, and highly efficient conjugation method for peptide-DNA coupling. In order to covalently couple peptides to nucleic acids, the peptides are prepared for reaction by modifying the N-terminal with a reactive group. In one embodiment, the N-terminal of the peptide is modified with S6H (succinimidyl-6-hydrazinonicotinateacetonehydrazone). N-protected, peptides are desalted and dissolved in dry DMF. Next, S6H is added in 2× molar excesses to a stirring, solution and allowed to react at room temperature for 2 hours. Workup follows procedures known in the art, such as that described by Dirksen et al. *J. Am. Chem. Soc.* 2006 128, 15602-3. Other methods of coupling peptides to nucleic acids known in the art may be used.

Figures 2A, 2B:
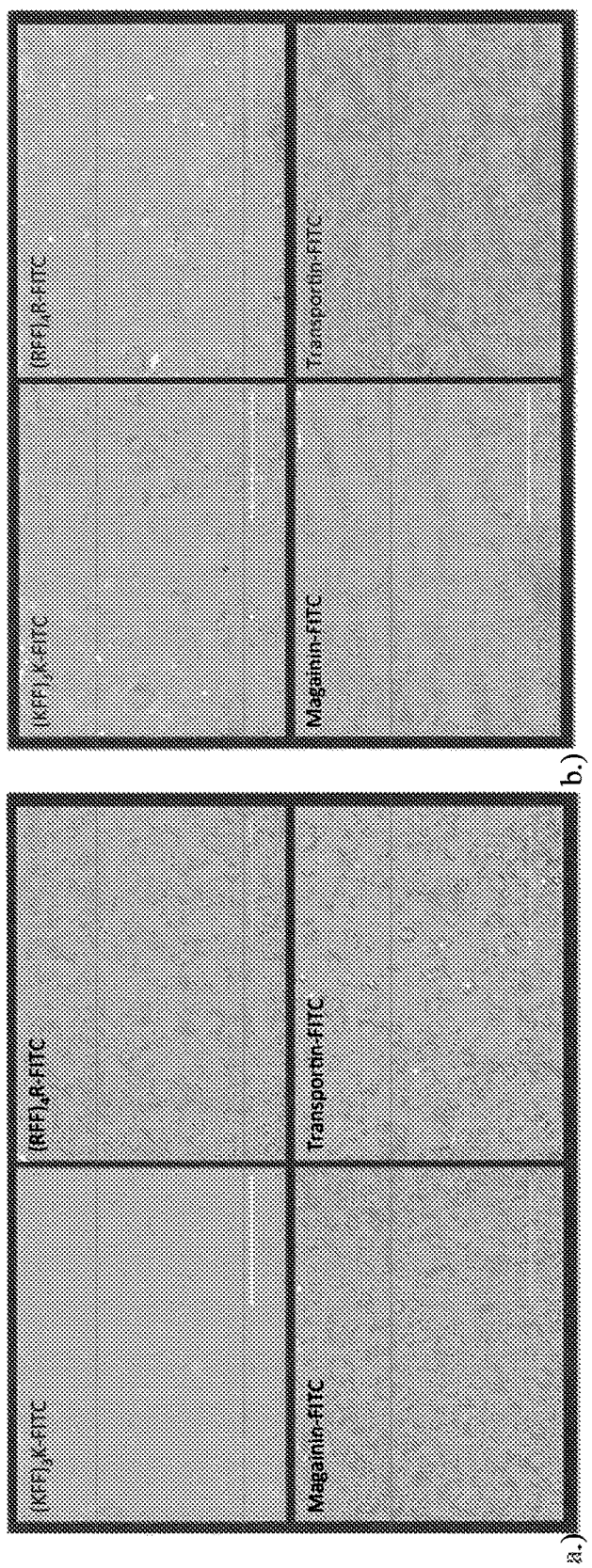
FIG. 2A-2B. a) MRSA fluorescent overlays 2 hours post treatment with 1 uM of FITC-peptide agents. b) AcB fluorescent overlays 2 hours post treatment with 1 uM of FITC-peptide agents. Scale bar=100 um. This figure shows that the cell-penetrating peptides are non-toxic when used alone.

An FITC assay may be utilized, to monitor cellular uptake of peptides. Peptides were conjugated to fluorescein isothiocyanate (FITC) to monitor uptake using florescence microscopy. FIG. 2A-2B show assay results for several peptides as tested in MRSA (FIG. 2A) and AcB (FIG. 2B) (fluorescent overlays 2 hours post-treatment with 1 μM of FITC peptide agents, scale bar=100 μm). For MRSA, the helical cationic peptides with KFF and RFF motifs are effective for cellular entry. Also, Magainin-FITC is effective for entry into MRSA. There do not appear to be any bactericidal effects from the peptides at the tested concentration (1 μM) in any of the micrographs presented in FIG. 2A-2B.

In another embodiment of the invention, the antisense molecule is combined with a delivery polymer. The polymer-based nanoparticle drug delivery platform is adaptable to a diverse set of polynucleotide therapeutic modalities. In one aspect of the invention, the delivery polymer is cationic. In another aspect of the invention, the delivery polymer comprises phosphonium ions and/or ammonium ions. In another example of the invention, the antisense molecule is combined with a delivery polymer, and the composition forms nanoparticles in solution. In a further embodiment, nanoparticle polyplexes are stable in serum and have a size in the range of about 30 nm-5000 nm in diameter. In one embodiment, the particles are less than about 300 nm in diameter. For example, the nanoparticles are less than about 150 nm in diameter.

In one embodiment, the delivery vehicle comprises a cationic block copolymer comprising phosphonium or ammonium ionic groups as described in PCT/US12/42974. In one embodiment, the polymer is diblock-Poly[(ethylene glycol)$_9$ methyl ethyl methacralate][stirylphosphonium]. In another embodiment of the invention, the delivery polymer comprises glycoamidoamines as described in Tranter et al. *Amer Soc Gene Cell Ther*, December 2011; polyhydroxylamidoamines, dendritic macromolecules, carbohydrate-containing polyesters, as described in US20090105115; and US20090124534. In other embodiments of the invention, the nucleic acid delivery vehicle comprises a cationic polypeptide or cationic lipid. An example of a cationic polypeptide is polylysine. See U.S. Pat. No. 5,521,291.

In one embodiment, the antisense molecules are part of a composition comprising delivery or carrier polymers. In another embodiment, the antisense molecules are part of nanoparticle polyplexes capable of transporting antisense molecules with stability in serum. The polyplex compositions comprise a synthetic delivery polymer (carrier polymer) and biologically active compound associated with one another in the form of particles having an average diameter of less than about 500 nm, such as about 300 nm, or about 200 nm, preferably less than about 150 nm, such as less than about 100 nm. The invention encompasses particles in the range of about 40 nm-500 nm in diameter.

In one embodiment, the delivery or carrier polymer comprises a cationic block copolymer containing phosphonium or ammonium ionic groups as described in PCT/US12/42974. In another embodiment of the invention, the delivery or carrier polymer comprises glycoamidoamines as described in Tranter et al. *Amer Soc Gene Cell Ther*, December 2011; polyhydroxylamidoamines, dendritic macromolecules, carbohydrate-containing polyesters, as described in US20090105115; and US20090124534. The polyglycoamidoamine (PGAA) polymer system, which is a proprietary, localized and biodegradable nanoparticle system, represents another delivery or carrier polymer. Poly (galactaramidoamine) is an efficient cationic polymeric vehicle with low cytotoxicity (Wongrakpanich et al. *Pharmaceutical Development and Technology*, Jan. 12, 2012). The nanoparticle delivery system disclosed in Hemp et al. *Biomacromolecules*, 2012 13:2439-45 represents another delivery or carrier polymer useful in the present invention.

In other embodiments of the invention, the delivery or carrier polymer comprises a cationic polypeptide or cationic lipid. Polymers, such as poly-L-lysine (PLL), polyethyleneimine (PEI), chitosan, and their derivatives are also encompassed by the invention. Nucleic acid delivery using these compounds relies on complexation driven by electrostatic interactions between the gene and the polycationic delivery agent. Polymer DNA complexes condense into particles on the order of 60 nm-120 nm in diameter. Polymers such, as linear PEI and PLL have high transfection rates in a variety of cells.

In vivo nucleic acid delivery has size constraints requiring a sufficiently small polyplex to enable long circulation times and cellular uptake. In addition, polyplexes must resist salt- and serum-induced aggregation. Serum stability is generally associated with a particle size of about sub-150 nm hydrodynamic radius or below maintainable for 24 h. The nanoparticles of the invention, which comprise nucleic acid therapeutic and delivery polymer, have the hydrodynamic radius and material properties for serum stability. In particular, the delivery polymer, when combined with the nucleic acid, protects the therapeutic cargo under physiological conditions. The delivery polymers are designed to have characteristics of spontaneous self-assembly into nanoparticles when combined with polynucleotides in solution.

The invention also contemplates other delivery polymers that form serum-stable nanoparticles. The invention is not limited to the type of delivery polymer and may be adaptable to nucleic acid characteristics, such as length, composition, charge, and presence of coupled peptide. The delivery polymer may also be adaptable for material properties of the resultant nanoparticle, such as hydrodynamic radius, stability, in the host bloodstream, toxicity to the host, and ability to release cargo inside a host cell.

In one embodiment, the antisense molecule or penetrating peptide conjugate thereof is administered in the form of a salt. The salt may be any pharmaceutically acceptable salt comprising an acid or base addition salt. Examples of pharmaceutically acceptable salts with acids include those formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic antisense molecules may be prepared by contacting the free base forms with a sufficient amount of the desired acid to produce the salt according to methods and techniques with which a skilled artisan is familiar.

Pharmaceutically acceptable base addition salts are formed by addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like.

The antisense molecules are administered as part of a pharmaceutical composition comprising a pharmaceutically acceptable diluent, excipient or carrier. Suitable diluents, excipients and carriers are well known in the art and are described, for example, in Remington's Pharmaceutical Sciences, Mack Publishing Co. (A.R. Gernnaro Ed., 1985). The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the antisense molecule in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The invention also provides a method of treating *Staphylococcus aureus* infection and a method of inhibiting the growth of *Staphylococcus aureus*. In one embodiment, the *Staphylococcus aureus* is a methicillin-resistant (MRSA) strain. In one embodiment, the animal undergoing treatment for *Staphylococcus aureus* infection exhibits one or more symptoms of *Staphylococcus aureus* infection including puss production in the infected area, boils, abscesses, carbuncles, stys, and/or cellulitis. The animal may also exhibit signs of sepsis or pneumonia.

In one embodiment, the antisense molecules are administered by intravenous, intramuscular, or peritoneal injection. In another embodiment, the antisense molecules are administered topically, e.g. to a tissue suspected to be infected by Staphylococcus aureus. In another embodiment, the antisense molecules are administered orally. When administered orally, the antisense molecules may be formulated as part of a pharmaceutical composition coated with an enteric coating that will protect the antisense molecules from the acid environment of the stomach and release the antisense molecules in the upper gastrointestinal tract. In another embodiment, the antisense molecules, may be formulated as part of a sustained release formulation that will release the antisense molecules on a substantially continuous basis over a period of time.

Animals that may be treated with the antisense molecules according to the invention include any animal that may benefit from treatment with the antisense molecules. Such animals include mammals such as humans, dogs, cats, cattle, horses, pigs, sheep, goats and the like.

The antisense molecules are administered in an amount that is effective for the treatment of Staphylococcus aureus infection or inhibition of the growth of Staphylococcus aureus. The amount may vary widely depending on the mode of administration, the age of the animal, the weight of the animal, and the surface area of the mammal. The amount of antisense molecule, conjugate, salt and/or complex thereof may range anywhere from 1 pmol/kg to 1 mmol/kg. In another embodiment, the amount may range from 1 nmol/kg to 10 mmol/kg. When administered topically, the amount of antisense molecule, conjugate, salt and/or complex thereof may range anywhere from 1 to 99 weight percent. In another embodiment, the amount of antisense molecule, conjugate, salt and/or complex thereof may range anywhere from 1 to 10 weight percent.

Example I

Synthesis of Peptide-PNA Conjugate:

All PNA agents were prepared using heterogenous solid-phase peptide synthesis techniques and purified with HPLC.

Although direct dosing with naked polynucleotides has been used to inhibit pathogenesis of MRSA in culture, a significant barrier for nucleic acid therapy in humans is the bacterial cell wall. To overcome the cell wall barrier, peptides derived from bacterial-infecting organisms that can penetrate these bacterial cell walls can be attached to nucleic acids or modified nucleic acids to enhance nucleic acid entry into the bacterium.

DNA sequences were synthesized using high-fidelity synthesizers made by NEO-Bio Group, Cambridge, Mass. The polynucleotide was then coupled to peptides which permit permeation of bacterial membranes and polynucleotide entry. In the present invention, solid-phase synthetic methodology for peptide-DNA coupling was employed where cysteine served as the linker between peptide and DNA.

In a specific embodiment, antisense 15-mer DNA and PNA analogs were synthesized for testing in cell culture. A positive control from literature (FmhB); and a noncoding sequence for use as a negative control (NC) were also synthesized. Each polynucleotide was coupled to the cell penetrating peptide (CPP) motif KFFKFFKFFK (SEQ ID NO: 51).

Both PNA-CPP and DNA-CPP candidates were synthesized and tested. Mass spectrometric analysis of each conjugate was performed to confirm successful synthesis. The purity of the PNA-peptide and DNA-peptide candidates was established using HPLC. Purity of about 99.9% was achieved for PNA-peptide; while >87% was achieved for DNA-peptide. DNA-peptides yielded a higher degree of impurity likely due to the steps required to make the DNA and CPP peptide separately and then conjugate them before a final purification step. Conversely, synthesis of the PNA agents yielded purity levels of about 99%. Increased purity and simplicity of manufacture of PNA-peptide therapeutics provides advantages over DNA-peptide candidates with respect to cGMP-compliant manufacture in battlefield arenas.

Example II

An FITC assay was utilized to monitor cellular uptake of peptides. Peptides were conjugated to fluorescein isothiocyanate (FITC) to monitor uptake using, florescence microscopy. FIG. 2A-2B shows assay results for several peptides as tested in MRSA (FIG. 2A) and AcB (FIG. 2B) (fluorescent overlays 2 hours post-treatment with 1 μM of FITC-peptide agents, scale bar=100 μm). For MRSA, the helical cationic peptides with KFF and RFF motifs are effective for cellular entry. Also, Magainin-FITC is effective for entry into MRSA. There do not appear to be any bactericidal effects from the peptides at the tested concentration (1 μM) in any of the micrographs presented in FIG. 2A-2B.

Example III

MRSA In Vitro Studies:

Demonstration of sequence-specific effects of PNA-peptide molecules on MRSA was carried out in MRSA USA 300. MRSA USA 300 is a major source of community-acquired infections in, the US, Canada and Europe. Clone FPR3757 is a multidrug-resistant USA 300 strain that is available from ATCC as both the culture (ATCC® BAA—1556TM) and the genomic DNA (ATCC® BAA—1556D-5). MRSA USA 300 strain is well characterized which allows for reliable benchmarking. MRSA growth curves were generated by inoculating freshly thawed frozen bacterial stocks at different dilutions ranging from 1:3000, 1:1500, 1:600 and 1:300 in Tryptic Soy Broth (TSB, Becton-Dickinson). Absorbance readings were taken hourly at 600 nm ($A_{600}$) and 550 nm ($A_{550}$) using a Biomate 3S spectrophotometer (Thermo Scientific) to establish optimal measurement settings and characterize bacterial growth kinetics. Readings at 550 nm gave slightly higher sensitivity. There was a correlation seen with the lower dilution titrations and a faster time to higher absorbance value. A550 was established as the optimal measurement to assess propagation in vancomycin titration and Minimum Inhibitory Concentration (MIC) assays.

Vancomycin titrations were established to determine a suitable test range. An 800 ug/ml stock solution was diluted tenfold in TSB to 80 ug/ml and further serial diluted to 40, 20, 10, 5, and 2.5 μg/ml in TSB, respectively. MRSA USA 300 strain was cultured to an early log phase OD 550 value of 0.111 and treated with the 80-2.5 μg/ml range of vancomycin. Absorbance measurements at 550 nm were taken hourly over a 4-hour time period.

Minimum inhibitory concentration (MIC) analyses were performed as described in Clinical and Laboratory Standards Institute. *Methods for Dilution Antimicrobial Susceptibility Tests for Bacteria that Grow Aerobically,* 7th ed.; Approved Standard M7-A7; CLSI: Wayne, Pa., USA, 2006; volume 26, No. 2. Vancomycin and methicillin were used as controls. MIC was determined as the lowest concentration of agent that inhibits bacterial growth detected at $A_{600}$.

Time-kill analyses were performed as described in Haste et al. *J. Antibiot.* 2010, 63, 219-224. Agents at various concentrations were aliquoted into the Falcon tubes. Four ml of bacteria at 5E5 cfu/ml were added to the tubes. Tubes were incubated in a shaker at 37° C., and at 0, 2, 4, and 8 h were subsequently analysed for bacterial growth via $A_{600}$.

Sequence-specific effects of polynucleotide-peptide agents against MRSA: A wide range of concentrations were tested for the PNA-peptide antisense sequences determined from bioinformatics. FmhB was used as a positive control from the literature (Xie et al., *Molecular Therapy*, 2004, 10, 652-659) and a non-encoding sequence with a terminal (KFF)$_3$K motif was used as a negative control (NC) to indicate bactericidal effects imparted by peptide membrane disruption. Sequence-specific inhibition was demonstrated by treating bacteria during lag phase to determine growth inhibition and potential recovery at later time points. The candidate agents and non-coding sequence control were diluted in a range from 20 µM, 5 µM, 1 µM, 250 µM, and 25 µM with sterile RNase-free, DNase-free water. Inhibition of MRSA growth was observed over a wide range of PNA-peptide concentrations.

Figure 3:
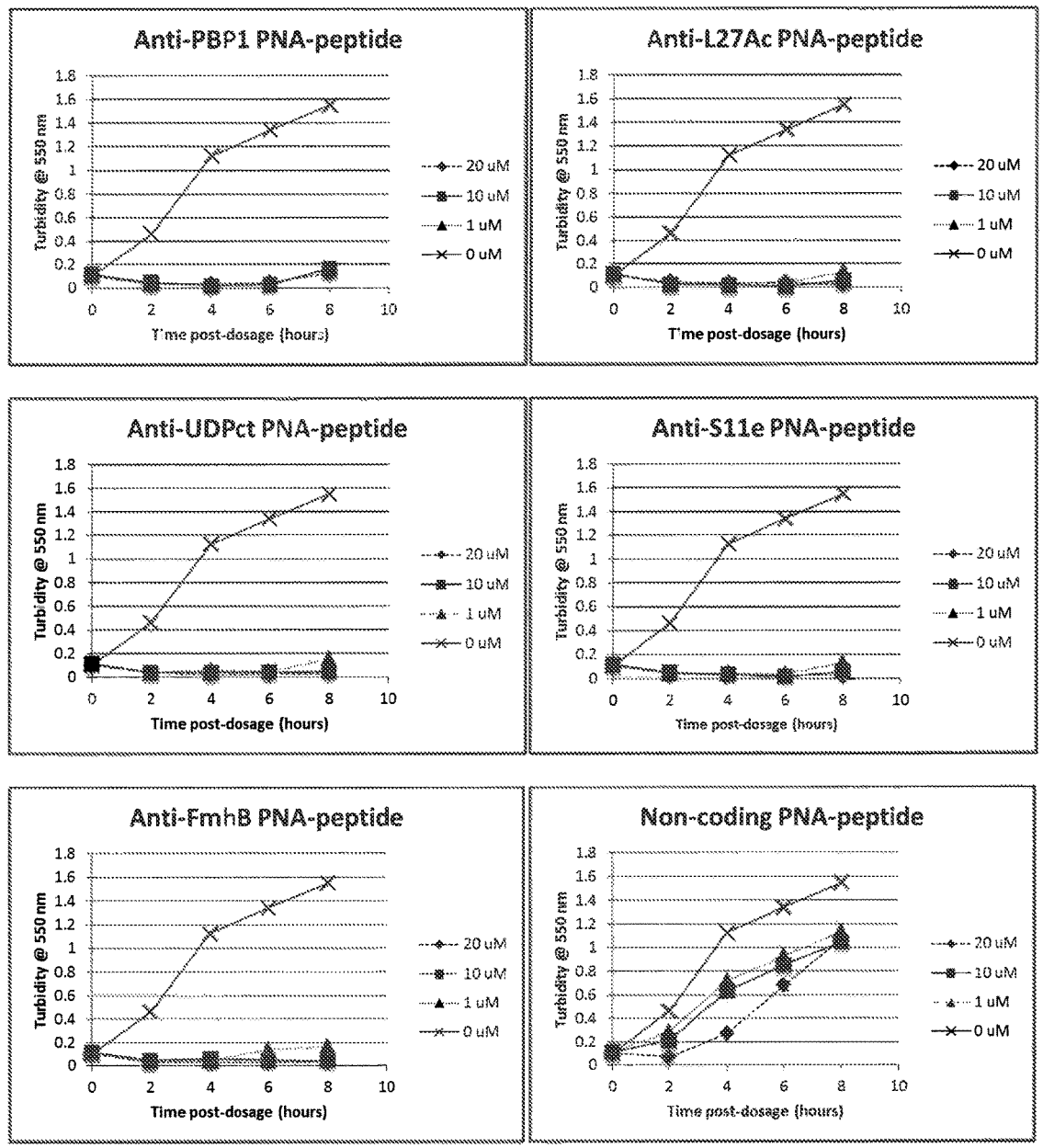
FIG. 3. Shows log-phase MRSA growth inhibition over 8 hours at 0 µM, 1 µM, 10 µM, and 20 µM concentration of PNA-peptide antisense antibiotic. Bottom left represents a positive control (FmhB) and bottom right shows a negative control.

The time course shown in FIG. 3 was carried out using MRSA strain USA 300. Freshly-thawed MRSA at a 1:100 dilution in TSB was added to wells containing the individual PNA-peptide molecules. An additional positive control, vancomycin at 12.5 ug/ml, and a negative control, water only, were also, assayed. The samples were allowed to incubate at 37° C. with 225 RPM orbital shaking and measured at two-hour time intervals, over an 8-hour time course. As FIG. 1 illustrates, inhibition of MRSA growth was observed over time at a 5 µM concentration.

In log-phase growth, inhibition is observed at concentrations as low as ~1 µM for PNA-peptide conjugates (FIG. 3) and as low as ~10 µM for DNA-peptide conjugates.

FIGS. 2A-2B demonstrate the non-toxicity of the cell-penetrating peptides. When conjugated to FITC and added to cells in culture, the cells remain alive over time periods of the cell culture experiments.

Example IV

To dissolve the DNA-peptide conjugates, they were dispersed in tris buffer at an elevated pH=9. The conjugates were then gently agitated for 24 h at 40° C. After this time period cloudiness was still observed, so the conjugates were heated to 80° C. under gentle agitation for an additional 6 h, after which clear solutions were obtained. The initial solution was tested via DLS to look at for potential self-assembly between the DNA-peptide conjugates. As exhibited with many charged polymers there was self-aggregation observed in solution, showing broad polydisperse aggregates in the 300 nm to 1-micron range.

Particle size plays an important role in determining blood circulation time and clearance. It is also a predictor of tissue permeation, clearance potential, and selectivity. Polymer-containing particles have been validated with siRNA and DNA, are capable of protecting nucleic acids from nuclease degradation, and can be engineered for colloidal stability in the bloodstream. The antisense molecule-peptide conjugates of the present invention were combined with serum-stable phosphonium-block copolymers to form polyplexes. This diblock copolymer forms a supramolecular assembly with negatively-charged DNA. The particle forms a core-shell type morphology with a neutral polyethylene glycol (PEG) brush on the surface. Polyplex hydrodynamic diameter was measured on a Zetasizer (Nano ZS) dynamic light scattering (DLS) instrument (Malvern Instruments, Worcestershire, UK). As a size comparison, a DNA-peptide conjugate (S11e-KFFKFFKFFK (SEQ ID NO: 51) without carrier polymer, was measured at 1 mg/ml in tris buffer solution at pH=9. This DNA-peptide conjugate with diblock-Poly[(ethylene glycol)$_9$ methyl ethyl methacralate][stirylphosphonium] at three concentrations exhibited size ranges from 40 nm-300 nm.

Formation of nanoparticles with the DNA-peptide conjugates is dependent on physical factors. Because the DNA region is negatively charged and the KFFKFFKFFK (SEQ ID NO 51) region is positively charged, the conjugates exhibit strong intramolecular associations in solution. A wide range of formulation conditions were evaluated. Optimal particles form at charge-to-charge ratios of 2-4 (phosphonium+/DNA phosphate−) and [DNA-peptide conjugate] ≤0.5 mg/ml and lower. When concentrations exceed 0.5 mg/ml, dynamic light scattering (DLS) analysis indicates that large aggregates form. The DLS data indicates that pre-formulation concentration influences the final nanoparticle size range, with 0.5 mg/ml forming the largest nanoparticles clustering around 90 nm-100 nm; and 0.1 mg/ml forming particles as small as 40 nm diameter.

To dissolve the DNA-peptide conjugates, they were dispersed in tris buffer at an elevated pH=9. The conjugates were then gently agitated for 24 h at 40° C. After this time period cloudiness was still observed, so the conjugates were heated to 80° C. under gentle agitation for an additional 6 h, after which clear solutions were obtained. The initial solution was tested via DLS to look at for potential self-assembly between the DNA-peptide conjugates. As exhibited with many charged polymers there was self-aggregation observed in solution, showing broad polydisperse aggregates in the 300 nm to 1 µm range.

All patents, patent applications and publications cited herein are fully incorporated by reference.

What is claimed is:

1. An antisense molecule or salt thereof that inhibits the growth of *Staphylococcus aureus* comprising a polynucleotide sequence that is antisense to the coding region of a *Staphylococcus aureus* ribosomal protein and hybridizes to said coding region under physiological conditions, wherein said antisense molecule is 10 to 50 nucleobases in length and has a sequence that is at least 95% identical to a sequence selected from the group consisting of SEQ ID NOs: 1, 2, 18-27, 29-46 and 48-50, and wherein said antisense molecule is conjugated to a cell penetration molecule.

2. The antisense molecule of claim 1, that has a sequence selected from the group consisting of SEQ ID NOs: 1, 2, 18-27, 29-46 and 48-50.

3. A pharmaceutical composition comprising the antisense molecule of claim 1 and a pharmaceutically acceptable diluent, excipient, or carrier, wherein the antisense molecule is 99-100% homogeneous by high-performance liquid chromatography (HPLC).

4. The antisense molecule of claim 1, wherein the antisense molecule comprises a modified backbone.

5. The antisense molecule of claim 4, wherein the modified backbone is a PNA backbone.

6. The antisense molecule of claim 1, which inhibits expression of LSU ribosomal protein L15p (L27Ae) or SSU ribosomal protein S17p (S11e), wherein the antisense molecule has a sequence selected from the group consisting of SEQ ID NOs: 1 and 2.

7. The antisense molecule of claim 1, wherein said cell penetration molecule is a peptide.

8. A composition comprising an antisense molecule of claim 1, complexed to a delivery polymer.

9. The composition of claim 8, wherein said delivery polymer is a cationic block copolymer comprising phosphonium or ammonium ionic groups.

10. A method of inhibiting the growth of *Staphylococcus aureus*, comprising administering an effective amount of an antisense molecule of claim 1 to a tissue containing said *Staphylococcus aureus* or suspected of containing *Staphylococcus aureus*.

11. The method of claim 10, comprising topical administration of the antisense molecule.

12. A method of treating *Staphylococcus aureus* infection, comprising administering to an animal in need thereof an effective amount of the antisense molecule of claim 1.

13. The method of claim 10, wherein said antisense molecule is complexed to a delivery polymer.

14. The method of claim 12, wherein said antisense molecule is complexed to a delivery polymer.

* * * * *